(12) United States Patent
Minai et al.

(10) Patent No.: US 9,439,558 B2
(45) Date of Patent: Sep. 13, 2016

(54) BODY-INTRODUCABLE APPARATUS AND MEDICAL SYSTEM

(75) Inventors: Tetsuo Minai, Tokyo (JP); Shinsuke Tanaka, Tokyo (JP); Tatsuya Orihara, Tokyo (JP); Yutaka Koshikawa, Tokyo (JP); Kazuaki Tamura, Tokyo (JP); Takeshi Mori, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 1232 days.

(21) Appl. No.: 12/775,810

(22) Filed: May 7, 2010

(65) Prior Publication Data

US 2010/0292534 A1 Nov. 18, 2010

Related U.S. Application Data

(63) Continuation of application No. PCT/JP2009/068319, filed on Oct. 26, 2009.

(30) Foreign Application Priority Data

Oct. 27, 2008 (JP) .................................. 2008-275860

(51) Int. Cl.
*A61B 1/04* (2006.01)
*A61B 1/06* (2006.01)
*A61B 1/00* (2006.01)

(52) U.S. Cl.
CPC ............. *A61B 1/041* (2013.01); *A61B 1/0638* (2013.01); *A61B 1/00016* (2013.01)

(58) Field of Classification Search
USPC ............................ 600/181, 178, 80; 362/574
See application file for complete search history.

(56) References Cited

U.S. PATENT DOCUMENTS

| 4,379,233 | A | * | 4/1983 | Rosenthal ..................... 250/553 |
| 4,580,552 | A | * | 4/1986 | Nishioka et al. ............. 600/177 |
| 4,610,513 | A | * | 9/1986 | Nishioka et al. ............... 385/33 |
| 4,671,630 | A | * | 6/1987 | Takahashi ..................... 359/503 |
| 5,835,648 | A | * | 11/1998 | Narciso et al. ................. 385/31 |
| 5,940,425 | A | * | 8/1999 | Lasser et al. ................... 372/72 |
| 6,364,829 | B1 | * | 4/2002 | Fulghum ....................... 600/160 |
| 6,638,215 | B2 | * | 10/2003 | Kobayashi .................... 600/160 |

(Continued)

FOREIGN PATENT DOCUMENTS

| JP | 10-337271 | 12/1998 |
| JP | 11-267099 | 10/1999 |

(Continued)

OTHER PUBLICATIONS

International Search Report dated Dec. 22, 2009.

(Continued)

*Primary Examiner* — Anhtuan T Nguyen
*Assistant Examiner* — William Chou
(74) *Attorney, Agent, or Firm* — Scully, Scott, Murphy & Presser, PC

(57) ABSTRACT

A body-introducable apparatus includes: a light source unit having a first light source that outputs first light and a second light source that outputs second light in a wavelength band different from that of the first light; a light distribution matching unit that matches distributions of the first light and the second light; an illuminating control unit that illuminates the inside of the subject by driving the light source unit; and an imaging unit that captures an image of the inside of the subject.

9 Claims, 15 Drawing Sheets

(56) References Cited

U.S. PATENT DOCUMENTS

| | | | |
|---|---|---|---|
| 6,690,466 B2* | 2/2004 | Miller et al. | 356/326 |
| 2002/0007111 A1* | 1/2002 | Deckert et al. | 600/177 |
| 2003/0015959 A1 | 1/2003 | Tomoda et al. | |
| 2003/0171653 A1* | 9/2003 | Yokoi et al. | 600/160 |
| 2005/0040424 A1* | 2/2005 | Erchak et al. | 257/100 |
| 2005/0043586 A1 | 2/2005 | Suzushima | |
| 2005/0088625 A1* | 4/2005 | Imade | 353/31 |
| 2008/0021281 A1* | 1/2008 | Fujimori | 600/160 |
| 2008/0027286 A1* | 1/2008 | Xie | 600/181 |
| 2008/0088701 A1* | 4/2008 | Unsai et al. | 348/65 |
| 2008/0284902 A1 | 11/2008 | Konno et al. | |
| 2008/0310181 A1* | 12/2008 | Gurevich et al. | 362/554 |
| 2009/0167149 A1* | 7/2009 | Ito | 313/501 |

FOREIGN PATENT DOCUMENTS

| | | |
|---|---|---|
| JP | 2002-112961 | 4/2002 |
| JP | 2003-260025 | 9/2003 |
| JP | 2004-243034 | 9/2004 |
| JP | 2005-304599 | 11/2005 |
| JP | 2006-136453 | 6/2006 |
| JP | 2006-247404 | 9/2006 |
| JP | 2006-297093 | 11/2006 |
| JP | 2007-59911 | 3/2007 |
| JP | 2007-181669 | 7/2007 |
| WO | WO 2005/071372 A1 | 8/2005 |

OTHER PUBLICATIONS

Extended Supplementary Partial European Search Report dated Mar. 16, 2015 from related European Application No. 09 82 3536.9.

* cited by examiner

BODY-INTRODUCABLE APPARATUS AND MEDICAL SYSTEM

CROSS-REFERENCE TO RELATED APPLICATIONS

This application is a continuation of PCT international application Ser. No. PCT/JP2009/068319 filed on Oct. 26, 2009 which designates the United States, incorporated herein by reference.

BACKGROUND OF THE INVENTION

1. Field of the Invention

The invention relates to a body-introducable apparatus and, more particularly, to a capsule-shaped body-introducable apparatus which is introduced into a subject such as human, animal, plant, or the like and captures an image of the inside of the subject.

2. Description of the Related Art

There is conventionally a capsule-shaped in-vivo imaging device for acquiring an image of the inside of a subject while illuminating the inside of the subject using a plurality of light sources outputting monotonous light or white light (refer to, for example, Japanese Application Patent Publication No. 2007-181669). In recent years, a technique of acquiring a color image of the inside of a subject by acquiring images of the inside of the subject while illuminating the inside of the subject using different light sources for red (R), green (G), and blue (B) is developed (refer to, for example, Japanese Application Patent Publication No. 2002-112961).

SUMMARY OF THE INVENTION

A body-introducable apparatus according to an aspect of the invention to be introduced in a subject, includes: a light source unit having a first light source that outputs first light and a second light source that outputs second light in a wavelength band different from that of the first light; a light distribution matching unit that matches distributions of the first light and the second light; an illuminating control unit that drives the light source unit to illuminate the inside of the subject; and an imaging unit that captures an image of the inside of the subject, wherein the light distribution matching unit includes a mirror that reflects the first and second light and a half mirror that reflects a part of the first and second light and transmits a part of the light, a reflection region is formed by disposing the mirror and the half mirror apart from each other, and the first and second light sources are disposed in the reflection region.

A body-introducable apparatus according to another aspect of the invention to be introduced in a subject, includes: a light source unit having a first light source that outputs first light and a second light source that outputs second light in a wavelength band different from that of the first light; a light distribution matching unit that matches distributions of the first light and the second light; an illuminating control unit that drives the light source unit to illuminate the inside of the subject; an imaging unit that captures an image of the inside of the subject; a circuit board on which the light source unit is mounted; and an optical window disposed on the side of a first face of the circuit board and transmitting light output from the light source unit to the outside, wherein the light source unit is mounted on a second face on the side opposite to the first face of the circuit board, and a through hole for passing the light output from the light source unit to the optical window is formed in the circuit board.

A body-introducable apparatus according to still another aspect of the invention to be introduced in a subject, includes: a light source unit having a light source that outputs first light and a wavelength shifter that converts a part of the first light to second light in a wavelength band different from that of the first light; a light distribution matching unit that matches distributions of the first light and the second light; an illuminating control unit that drives the light source unit to illuminate the inside of the subject; and an imaging unit that captures an image of the inside of the subject, wherein the wavelength shifter has a plurality of through holes for making the first light output from the light source dispersedly pass.

A body-introducable apparatus according to still another aspect of the invention to be introduced in a subject, includes: a light source unit having a light source that outputs first light and second light in a wavelength band different from that of the first light, a first filter that transmits the first light, and a second filter that transmits the second light; a light distribution matching unit that matches distributions of the first light and the second light; an illuminating control unit that drives the light source unit to illuminate the inside of the subject; and an imaging unit that captures an image of the inside of the subject, wherein the first and second filters make the first and second light output from the light source dispersedly pass, respectively.

A body-introducable apparatus according to still another aspect of the invention to be introduced in a subject, includes: a light source unit having a light source that outputs first light, a white light source that outputs white light and transmits the first light, and a wavelength shifter that converts a part of the first light to second light in a wavelength band different from that of the first light; a light distribution matching unit that matches distributions of the first light, the second light, and the white light; an illuminating control unit that drives the light source unit to illuminate the inside of the subject; and an imaging unit that captures an image of the inside of the subject, wherein the light source and the white light source are disposed such that their optical axes match each other.

A medical system according to still another aspect of the invention includes: a body-introducable apparatus including a light source unit having a first light source that outputs first light and a second light source that outputs second light in a wavelength band different from that of the first light, a light distribution matching unit that matches distributions of the first light and the second light, an illuminating control unit that drives the light source unit to illuminate the inside of the subject, and an imaging unit that captures an image of the inside of the subject, the light distribution matching unit including a mirror that reflects the first and second light and a half mirror that reflects a part of the first and second light and transmits a part of the light, a reflection region being formed by disposing the mirror and the half mirror apart from each other, and the first and second light sources being disposed in the reflection region; a communication device disposed on the outside of the subject; and a display device that displays an image by using image data, wherein the body-introducable apparatus has a wireless transmitting unit that transmits image data obtained by the imaging unit as a wireless signal, the communication device includes a wireless receiving unit that receives the image data transmitted from the wireless transmitting unit, an image signal processing unit that processes the image data received by the wireless receiving unit, and a communication device external interface unit that stores the image data processed by the image signal processing unit to a portable recording medium detachably connected to the communication device, and the display device includes a display device external interface unit to which the portable recording medium can be detachably connected, and a display unit that reads the image data from the portable recording medium connected to the display device external interface unit and displays the read image data.

A medical system according to still another aspect of the invention includes: a body-introducable apparatus including a light source unit having a first light source that outputs first light and a second light source that outputs second light in a wavelength band different from that of the first light, a light distribution matching unit that matches distributions of the first light and the second light, an illuminating control unit that drives the light source unit to illuminate the inside of the subject, and an imaging unit that captures an image of the inside of the subject, the light distribution matching unit including a mirror that reflects the first and second light and a half mirror that reflects a part of the first and second light and transmits a part of the light, a reflection region being formed by disposing the mirror and the half mirror apart from each other, and the first and second light sources being disposed in the reflection region; a communication device disposed on the outside of the subject; and a display device that displays an image by using image data, wherein the body-introducable apparatus has a wireless transmitting unit that transmits image data obtained by the imaging unit as a wireless signal, the communication device includes a wireless receiving unit that receives the image data transmitted from the wireless transmitting unit, an image signal processing unit that processes the image data received by the wireless receiving unit, and a communication device external interface unit that outputs the image data processed by the image signal processing unit to the display device, and the display device includes a display device external interface unit that inputs the image data output from the communication device external interface unit, and a display unit that displays an image of the inside of the subject by using the image data which is input to the display device external interface unit.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Figure 1:
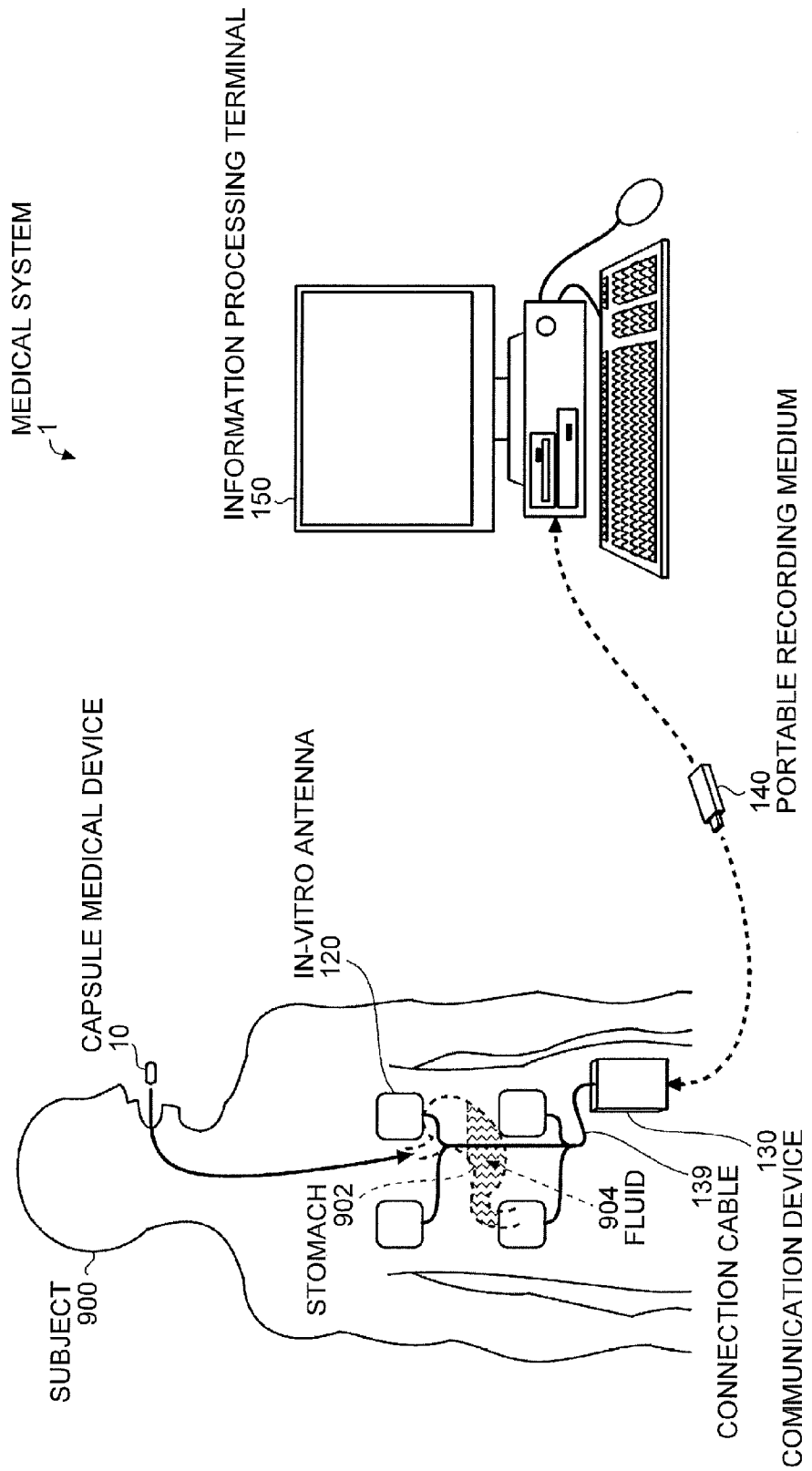
FIG. 1 is a schematic diagram illustrating a schematic configuration of a medical system using a capsule medical device according to any of first to seventh embodiments of the invention.

Best modes for carrying out the invention will be described in detail below with reference to the drawings. In the following description, the drawings schematically illustrate shapes, sizes, and positional relations to a degree that the content of the invention can be understood. Therefore, the invention is not limited to the shapes, sizes, and positional relations illustrated in the drawings. In the drawings, to clearly illustrate the configuration, a part of hatching in cross sections is omitted. Further, numerical values exemplified in the following description are just preferable examples of the invention. Therefore, the invention is not limited to the numerical values exemplified.

First Embodiment

First, a capsule medical device 10 according to a first embodiment of the invention will be described in detail with reference to the drawings. In the embodiment, the case of acquiring an image of the inner wall of a stomach 902 by applying the capsule medical device 10 as a body-introducable apparatus floating in a fluid 904 in the stomach 902 will be described as an example. However, the invention is not limited to the case. The capsule medical device 10 of the embodiment can be also applied as a body-introducable apparatus for acquiring an image of the inside of a subject 900 during travel from the esophagus to the anus. An organ that accumulates the fluid 904 is not limited to the stomach 902 but may be various organs such as small intestine and large intestine. Further, it is preferable to use, as the fluid 904, a fluid which does not exert adverse influence on the subject 900 and the capsule medical device 10 such as saline or water. Preferably, the fluid 904 is transparent. Consequently, an image acquired by the capsule medical device 10 can be prevented from becoming unclear due to the fluid 904.

FIG. 1 is a schematic diagram illustrating a schematic configuration of a medical system 1 using the capsule medical device 10 according to the embodiment. As illustrated in FIG. 1, the system has: the capsule medical device 10 which is, for example, orally introduced into the subject 900 and floating in the fluid 904 accumulated in the stomach 902, and a communication device 130 for transmitting/receiving image data and a control instruction, and the like to/from the capsule medical device 10 by performing wireless communication with the capsule medical device 10.

To the communication device 130, a portable recording medium 140 such as a flash memory (registered trademark) and a smart card (registered trademark) is detachably attached. In the portable recording medium 140, for example, image data of an in-vivo image of the subject acquired by the capsule medical device 10 is recorded. The user connects the portable recording medium 140 to an information processing terminal 150 such as a personal computer or a server, reads the image data stored in the portable recording medium 140 by the information processing terminal 150, and displays the in-vivo image on a display unit of the information processing terminal 150.

The communication device 130 is disposed on the outside of the subject 900. To the communication device 130, an in-vitro antenna 120 is connected via a connection cable 139 such as a coaxial cable. The in-vitro antenna 120 is disposed out of the subject 900 and near the capsule medical device 10. The communication device 130 transmits/receives data to/from the capsule medical device 10 via the in-vitro antenna 120.

Figure 2:
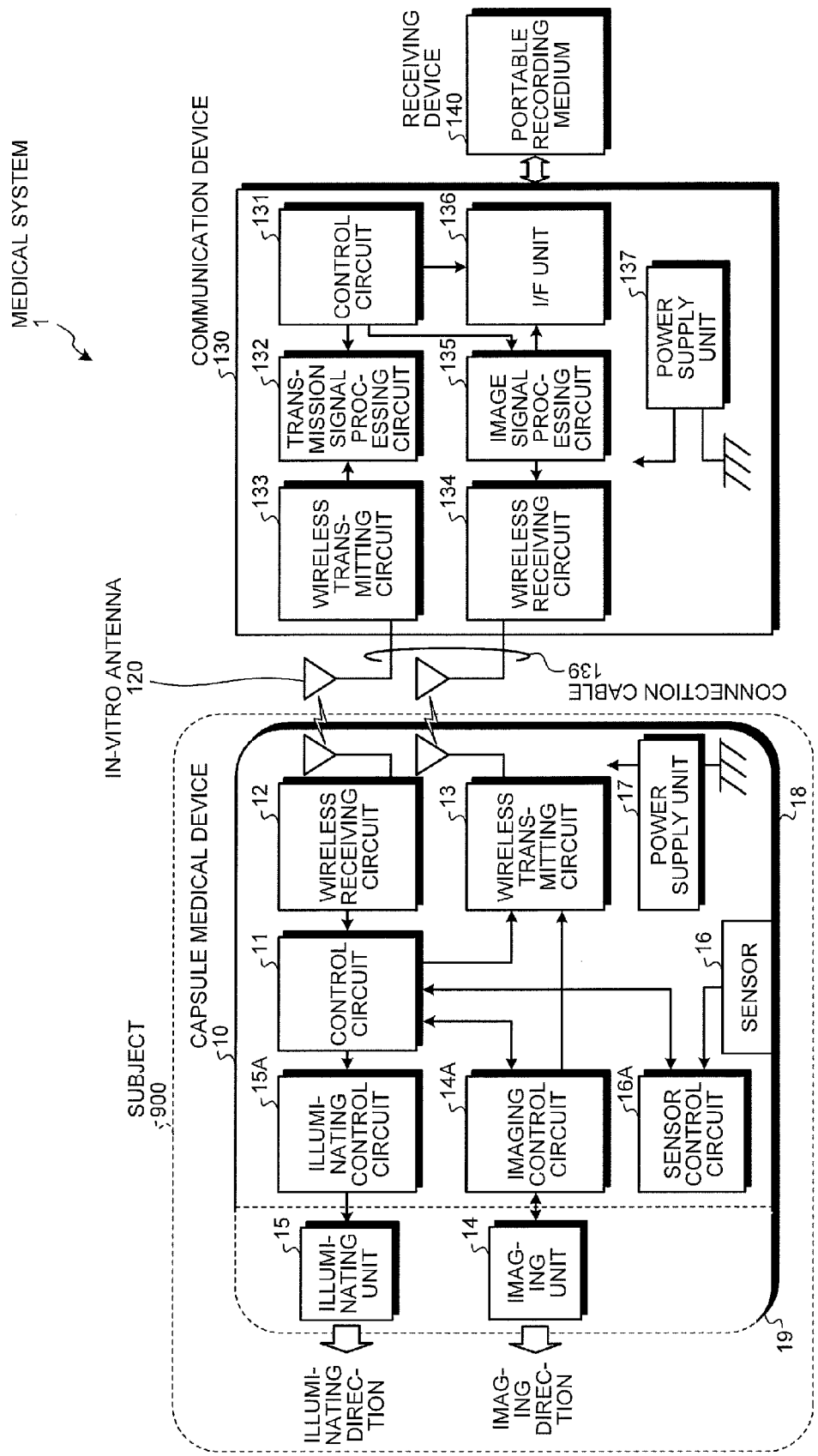
FIG. 2 is a block diagram illustrating a schematic configuration of devices as components of the medical system according to any of the first to sixth embodiments of the invention.
Figure 3:
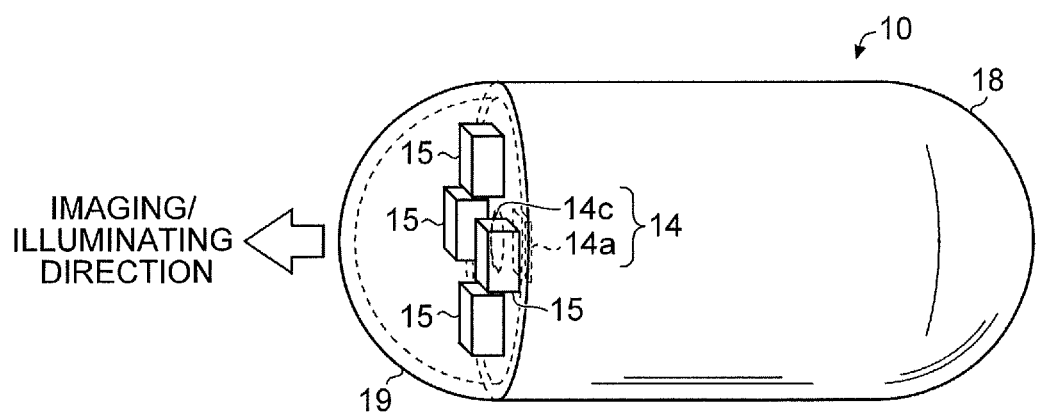
FIG. 3 is a perspective view illustrating a schematic configuration of the capsule medical device according to any of the first to seventh embodiments of the invention.
Figure 4:
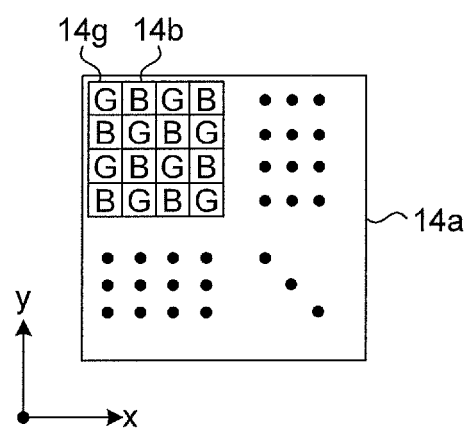
FIG. 4 is a conceptual diagram illustrating an example of an array of imaging elements in an imaging unit in the capsule medical device according to any of the first to sixth embodiments of the invention.

With reference to FIGS. 2 to 4, the medical system 1 according to the embodiment will be described more specifically. FIG. 2 is a block diagram illustrating a schematic configuration of devices as components of the medical system 1 according to the embodiment. FIG. 3 is a perspective view illustrating a schematic configuration of the capsule medical device 10 according to the embodiment. FIG. 4 is a block diagram illustrating a schematic configuration of an image signal processing device 135 in the communication device 130 according to the embodiment. FIG. 4 is a conceptual diagram illustrating an example of an array of imaging elements 14a in an imaging unit 14 in the capsule medical device 10.

Capsule Medical Device

First, an example of the capsule medical device 10 according to the embodiment will be described in detail with reference to FIG. 2. As illustrated in FIG. 2, the capsule medical device 10 introduced in the subject 900 has: the imaging unit 14 for capturing an image of the inside of the subject 900; an imaging control circuit 14A for acquiring image data by driving the imaging unit 14; a plurality of illuminating units 15 for outputting light in a plurality of wavelength bands; an illumination control circuit 15A for illuminating the imaging direction by driving the illuminating units 15 at the time of capturing an image of the inside of the subject 900 by the imaging unit 14; a wireless transmitting circuit 13 for transmitting the image data captured by the imaging control circuit 14A as a wireless signal to the communication device 130; a wireless receiving circuit 12 for receiving a wireless signal transmitted from the communication device 130; a control circuit 11 for controlling the circuits in the capsule medical device 10 on the basis of a control instruction and the like input from the communication device 130 via the wireless receiving circuit 12; and a power supply unit 17 for supplying power to the circuits in the capsule medical device 10. The configuration and layout of the imaging unit 14 and the illuminating unit 15 will be described in detail later.

The control circuit 11 drives the imaging control circuit 14A and the illuminating control circuit 15A to execute imaging operation periodically (for example, two frames per second) on the basis of a control instruction or the like received from the communication device 130 via the wireless receiving circuit 12, and causes the wireless transmitting circuit 13 to transmit image data acquired by the imaging operation to the communication device 130.

Further, the capsule medical device 10 may have a sensor 16 and a sensor control circuit 16A for controlling the sensor 16. The sensor 16 includes a thermometer, a pressure meter, a pH meter, and the like and properly obtains temperature, pressure, pH value, and the like in the subject 900 as subject in-vivo information. The sensor control circuit 16A drives the sensor 16 to obtain in-vivo information of the subject and inputs it to the control circuit 11 under control of the control circuit 11.

The circuits and units in the capsule medical device 10 are, as illustrated in FIG. 2, housed in a capsule-shaped casing formed of a container 18 and a cap 19. As illustrated in FIG. 3, the container 18 has one end, which is a hemispherical dome shape, and the other end, which is opened, and has almost-cylindrical or semielliptical shape. The cap 19 has a hemispherical shape and is fit in the opening of the container 18, thereby sealing the container 18. The capsule container formed of the container 18 and the cap 19 has, for example, a size to a degree that it can be swallowed by the subject 900. In the embodiment, at least the cap 19 is formed of a transparent material, and the imaging unit 14 and the illuminating unit 15 are disposed on the side of the cap 19 in the capsule container (18, 19). The imaging direction of the imaging unit 14 and the illuminating direction of the illuminating unit 15 correspond to the direction toward the outside of the capsule medical device 10 via the cap 19, as illustrated in FIG. 2 or FIG. 3. With the configuration, an image of the inside of the subject 900 can be captured by the imaging unit 14 while illuminating the inside of the subject 900 by the illuminating unit 15. The cap 19 also has the function as a lens for adjusting distribution of light output from the illuminating unit 15 and/or light incident on the imaging element 14a via an objective lens 14c.

Communication Device

Next, an example of the communication device 130 according to the embodiment will be described in detail with reference to FIGS. 2 and 4. As illustrated in FIG. 2, the communication device 130 disposed on the outer surface of the subject 900 (for example, the surface of the subject 900, cloth of the subject 900, or the like) has: a control circuit 131 for controlling generation of a transmission signal such as a control instruction, storage of image data received from the capsule medical device 10 to the portable recording medium 140, and the like; a transmission signal processing circuit 132 for generating a transmission signal by executing a predetermine process on the control instruction of the capsule medical device 10 output from the control circuit 131 or the like; a wireless transmitting circuit 133 for transmitting the transmission signal from the in-vitro antenna 120; a wireless receiving circuit 134 for receiving image data or the like transmitted from the capsule medical device 10 via the in-vitro antenna 120; the image signal processing circuit 135 for generating an image signal (also called image data) by executing a predetermined process on the received image data; an interface circuit 136 to which the portable recording medium 140 can be detachably attached; and a power supply unit 137 for supplying power to the units in the communication device 130.

The communication device 130 may be provided with an operation unit for inputting various operations such as an imaging instruction by the operator or can perform communication with another device having the operation unit via a wireless circuit or wired circuit. Further, the communication device 130 may be provided with a display unit for displaying a subject's in-vivo image received from the capsule medical device 10.

Imaging Unit and Illuminating Unit

Figure 5A:
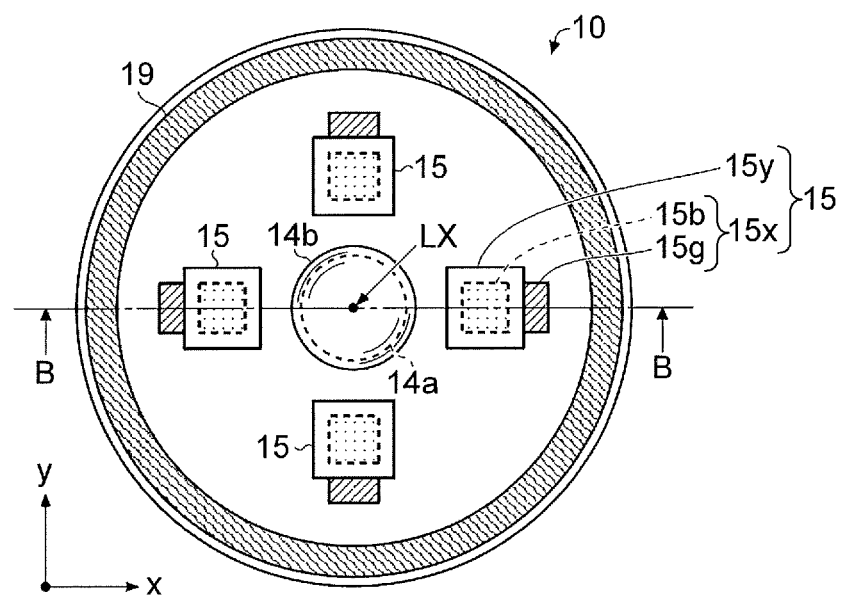
FIG. 5A is a diagram illustrating a configuration example of the capsule medical device according to the first embodiment of the invention.
Figure 5B:
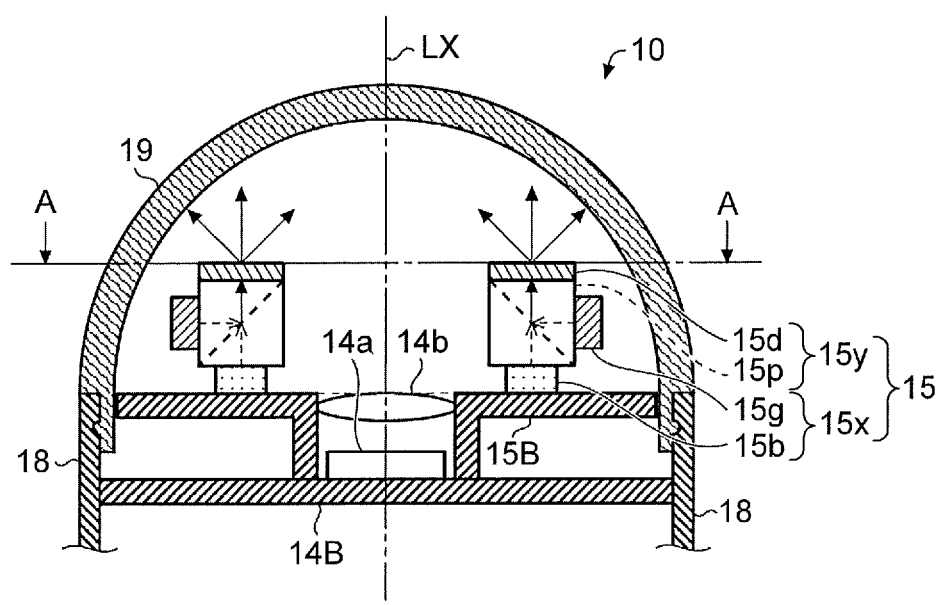
FIG. 5B is a cross section taken along line B-B in FIG. 5A.
Figure 6:
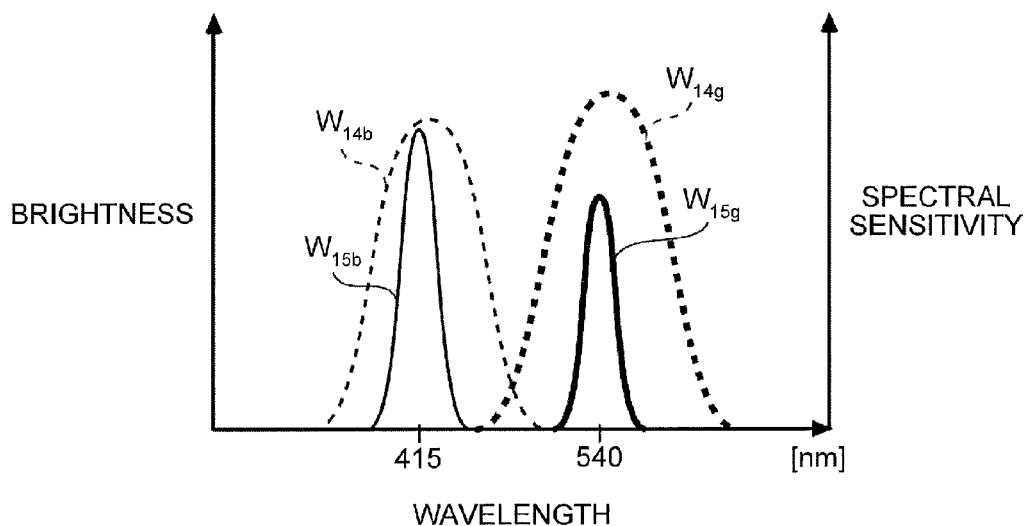
FIG. 6 is a diagram illustrating a light-emitting characteristic of an illuminating unit and a spectral sensitivity characteristic of an imaging element according to the first to sixth embodiments of the invention.
Figure 7:
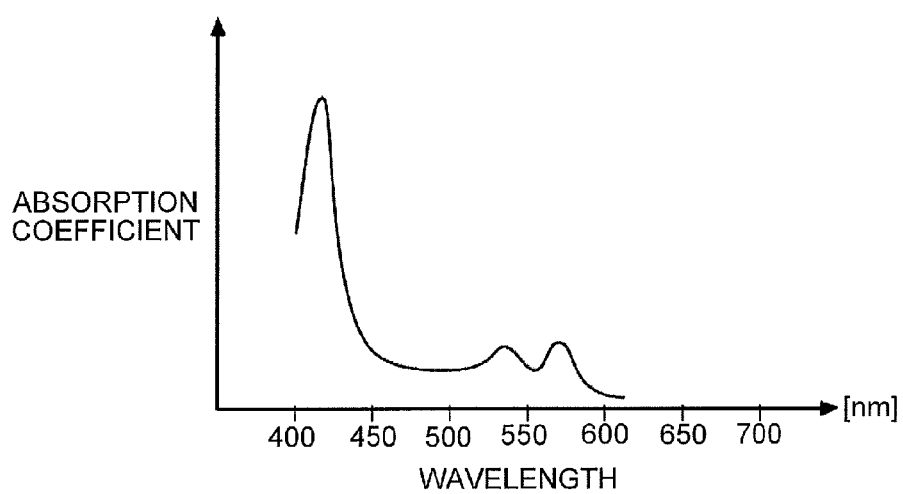
FIG. 7 is a diagram illustrating an absorbance characteristic of blood.

Next, a more-detailed configuration example of the imaging unit 14 and the illuminating unit 15 in the capsule medical device 10 according to the embodiment will be described specifically by using the drawings. FIG. 4 is a layout diagram illustrating an example of an array of the imaging elements 14a in the imaging unit 14 according to the embodiment. FIGS. 5A and 5B are diagrams illustrating a configuration example of the capsule medical device 10 according to the embodiment. FIG. 5A is a cross section taken along line A-A in FIG. 5B, and FIG. 5B is a cross section taken along line B-B in FIG. 5A. FIG. 6 illustrates a light-emitting characteristic of the illuminating unit 15 and the spectral sensitivity characteristic of the imaging element 14a. As an example, FIG. 7 illustrates an absorbance characteristic of blood.

In the embodiment, the case of performing so-called special-light observation of capturing an image by driving the imaging unit 14 while illuminating the inside of the subject 900 with light in a wavelength band as a part of a visible region (hereinbelow, called special light) will be described as an example. In the embodiment, imaging performed by driving the imaging unit 14 while illuminating the inside of the subject 900 with light in the wavelength band in the entire visible region, so-called white light (hereinbelow, called normal light) will be called normal-light observation.

Imaging Unit

As illustrated in FIG. 3, the imaging unit 14 according to the embodiment has the imaging element 14a receiving reflection light from the inner wall of the subject 900 and accumulating charges, and the objective lens 14c disposed on the light reception plane side of the imaging element 14a. The imaging unit 14 is mounted on a circuit board 14B having the imaging control circuit 14A for controlling the imaging unit 14. The circuit board 14B is disposed near to the cap 19 side in a state where the surface on which the imaging unit 14 is mounted is directed toward the cap 19 side.

The imaging control circuit 14A drives the imaging unit 14 to acquire image data of an image in the subject and inputs it to the wireless transmitting circuit 13 under control of the control circuit 11. The imaging control circuit 14A generates, for example, digital image data by executing predetermined processes such as sampling, amplification, and Analog-to-Digital (A/D) conversion on the analog image data input from the imaging unit 14.

As illustrated in FIG. 4, the imaging element 14a is a Charge Coupled Device (CCD) or Complementary Metal Oxide Semiconductor (CMOS) camera in which a plurality of light receiving elements 14b and a plurality of light receiving elements 14g are arranged alternately in row and column directions (x and y directions in the diagram). As illustrated in FIG. 6, the light receiving element 14b receives, for example, light in a wavelength band $W_{14b}$ around 415 nm and accumulates charges. On the other hand, the light receiving element 14g receives, for example, light in a wavelength band $W_{14g}$ around 540 nm. Therefore, image data acquired using the imaging element 14a includes image data generated by the light receiving element 14b which receives light in the wavelength band $W_{14b}$ around 415 nm and image data generated by the light receiving element 14g which receives light in the wavelength band $W_{14g}$ around 540 nm. Light in the wavelength band $W_{14b}$ around 415 nm displays blue, and light in the wavelength band $W_{14g}$ around 540 nm displays green. Therefore, the imaging element 14a generates image data of a green (G) component and image data of a blue (B) component.

In the case where the subject 900 is a living body such as human or animal, as illustrated in FIG. 7, the absorbance of blood has peaks around 415 nm and around 540 nm. Therefore, by generating image data of a positive image by inverting image data of a so-called negative image obtained by receiving reflection light of light around 415 nm and light around 540 nm by the imaging element 14a, an image expressing the structure of blood vessels of the subject 900 can be generated.

The transmittance of light generally varies according to the wavelengths. Since light in two kinds of wavelength bands of light around 415 nm and light around 540 nm is used in the embodiment, by using image data generated from a reflection component of the light around 415 nm and image data generated from a reflection component of the light around 540 nm, a stereoscopic image expressing a stereoscopic structure of the blood vessels can be generated.

Illuminating Unit

Each of the illuminating units 15 according to the embodiment includes a light source made by one or more Light Emitting Diodes (LEDs) outputting light in different wavelength bands, and is mounted on a circuit board 15B having the illuminating control circuit 15A for controlling the light source. For example, the illuminating control circuit 15A drives the illuminating unit 15 to illuminate the inside of the subject 900 synchronously with an image capturing timing under control of the control circuit 11.

In the embodiment, as illustrated in FIG. 5A, for example, a plurality of illuminating units 15 are disposed on the circuit board 15B on which the illuminating control circuit 15A is mounted so as to be point-symmetrical with respect to one point on the optical axis LX of the objective lens 14c as a center. The invention, however, is not limited to the layout. The plurality of illuminating units 15 may be disposed, for example, on the circuit board 15B so as to be line-symmetrical with respect to a straight line, as a center line, including one point on the optical axis LX and parallel to the x axis or y axis of image data (refer to FIG. 4 and FIG. 5A) obtained by the imaging element 14a.

Each of the illuminating units 15 has, as illustrated in FIGS. 5A and 5B and FIG. 6, for example, a light source 15x including an LED 15b (first light source) outputting light in the wavelength band $W_{15b}$ around 415 nm (hereinbelow, called "first special light") and an LED 15g (second light source) outputting light in the wavelength band $W_{14g}$ around 540 nm (hereinbelow, called "second special light"). Referring to FIG. 6, the relations among the wavelength band of the first special light output from the LED 15b, the wavelength band of the second special light output from the LED 15g, the light reception sensitivity band of the light receiving element 14b, and the light reception sensitivity band of the light receiving element 14g will be described. As illustrated in FIG. 6, in the embodiment, the LED 15b outputs the first special light in the wavelength band $W_{15b}$ having a peak around 415 nm, and the light receiving sensitivity band $W_{14b}$ of the light receiving element 14b has a peak around 415 nm. Consequently, the light receiving element 14b mainly receives dispersion of the first special light output from the LED 15b and generates image data. On the other hand, the LED 15g outputs second special light in the wavelength band $W_{15g}$ having a peak around 540 nm, and the light reception sensitivity band $W_{14g}$ of the light receiving element 14g has a peak around 540 nm. Consequently, the light receiving element 14g mainly receives dispersion of the second special light output from the LED 15g, and generates image data.

Each of the illuminating units 15 has a light distribution matching unit 15y made by a dichroic prism 15p for combining the first and second special light so that the optical axis of the first special light output from the LED 15b and the optical axis of the second special light output from the LED 15g overlap, and a diffuser 15d for diffusing the combined light output from the dichroic prism 15p, thereby matching distributions of the first and second special light. Match of light distributions denotes that light distributions in the case of normalizing light in different wavelength bands with maximum illuminance match or almost match regardless of the fact that the maximum illuminance is the same or not. The optical axis of the LED denotes that a center line of light distribution output from LED.

Figure 8:
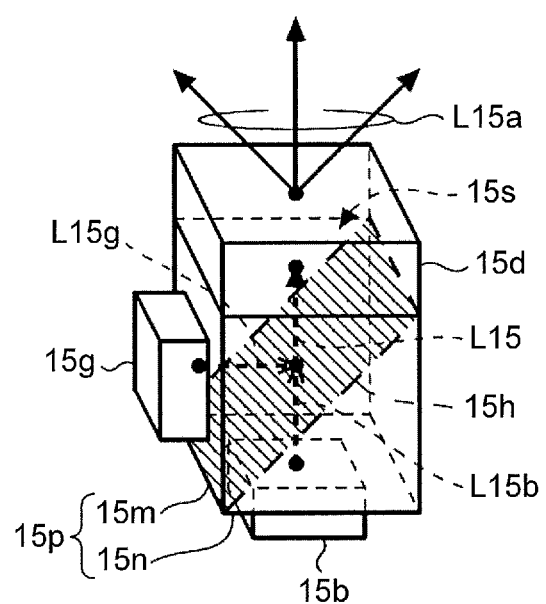
FIG. 8 is a perspective view illustrating a schematic configuration of a light distribution matching unit according to the first embodiment of the invention.

FIG. 8 illustrates a schematic configuration of the light distribution matching unit 15y. As illustrated in FIG. 8, the dichroic prism 15p has a cubic or rectangular-parallelepiped shape and has, at least, a first member 15m that transmits first special light L15b and second special light L15g, and a second member 15n that transmits the first special light L15b and reflects the second special light L15g. Each of the first and second members 15m and 15n has a triangular prism shape whose section has an isosceles right triangle. The dichroic prism 15p is obtained by joining the faces, each of which has the hypotenuse of the isosceles right triangles, of the first and second members 15m and 15n. The joined face functions as a reflection face 15h for reflecting the second special light L15g. The LEDs 15b and 15g of the light source 15x are disposed on faces each having a tilt of 45° with respect to the reflection face 15h, which is the joined face of the first and second members 15m and 15n in the dichroic prism 15p, and emit the first special light L15b and the second special light L15g, respectively, toward the center of the dichroic prism 15p.

In the embodiment, as illustrated in FIG. 8, the LED 15g is disposed in an almost center of a side face of the first member 15m of the dichroic prism 15p, and the LED 15b is disposed in an almost center of the bottom face of the second member 15n of the dichroic prism 15p. With such a configuration, the first special light L15b output from the LED 15b is transmitted by the reflection face 15h at the joined face and travels toward a light outgoing face 15s, and the second special light L15g output from the LED 15g is reflected by the reflection face 15h and travels toward the light outgoing face 15s. Consequently, the first and second special light L15b and L15g can be combined at the reflection face 15h. For example, the optical axis of combined light L15 passes through the center of the light outgoing face 15s, which is the top face of the dichroic prism 15p, and is parallel to the optical axis LX of the objective lens 14c.

As described above, the diffuser 15d is disposed on the light outgoing face 15s of the dichroic prism 15p. The light incident face and the light outgoing face of the diffuser 15d are opposed to each other and are, for example, subjected to sandblast process. In each of the light incident face and the light outgoing face of the diffuser 15d, a number of projections and depressions are formed. By disposing the diffuser 15d forming the region sandwiched by the two faces having a number of projections and depressions on the light outgoing face 15s of the dichroic prism 15p, the combined light L15 incident on the diffuser 15d can be diffusely reflected a plurality of times by the light incident face and the light outgoing face of the diffuser 15d. Therefore, each of the first and second special light L15b and L15g included in the combined light L15 can be diffused. As a result, the distribution of the first special light L15b and that of the second special light L15g included in the combined light L15a output from the light outgoing face of the diffuser 15d can be matched.

The configuration of matching the distribution of the first special light L15b and that of the second special light L15g included in the combined light L15 output from the dichroic prism 15p is not limited to the diffuser 15d but may be variously modified to, for example, a plate-shaped waveguide having a refractive index different from that of the dichroic prism 15p and that of atmosphere in the capsule medical device 10.

With the configuration as described above, in the embodiment, light in different wavelength bands having the matched optical axis and the matched distribution (the first and second special light) can be output from each of the illuminating units 15. In the capsule medical device 10 according to the embodiment, the plurality of illuminating units 15 are arranged (refer to, for example, FIG. 5A) point-symmetrically using one point on the optical axis LX of the objective lens 14c as a center or line-symmetrically using a straight line passing through one point on the optical axis LX as a center line. Consequently, in the case of simultaneously driving the plurality of illuminating units 15, the optical axes and distributions of the entire light in the different wavelength bands output from the entire illuminating units 15 to the image capturing direction can be made matched.

By illuminating the inside of the subject 900 with light in different wavelength bands and whose optical axes and distributions are matched as described above, the brightness distributions of image data of color components obtained by the imaging unit 14 can be made coincide. As a result, image data of an in-vivo image of the subject with reduced color unevenness can be generated.

Further, in the embodiment, the cap 19 as an optical window of the capsule medical device 10 has the optical function of adjusting the distribution of light passing through the cap 19. Therefore, the optical axes and distributions of light in different wavelength bands can be further matched.

Although the LED 15b outputting light having the peak around 540 nm is used as the light source of the second special light in the embodiment, the invention is not limited to the case. For example, it is also possible to use a light source obtained by combining a white LED which emits normal light and a filter which transmits/outputs light around 540 nm by making a part of the light emitted from the white LED pass through or shifting the wavelength.

First Modification

Although the configuration that the illuminating unit 15 is disposed on the face on the cap side 19 of the circuit board 15B on which the illuminating control circuit 15A is mounted has been described in the embodiment, the invention is not limited to the configuration. For example, a configuration that the illuminating unit 15 is disposed on the face, which is opposite from the cap 19, of the circuit board 15B (the face will be called a rear face) as illustrated in a capsule medical device 10A as a first modification of the embodiment illustrated in FIGS. 9A and 9B may be employed. In this case, in the circuit board 15B, an opening 15a for emitting light output from the diffuser 15d toward the cap 19 side is formed.

With the configuration that the illuminating unit 15 on the rear face side of the circuit board 15B, the distance between the illuminating unit 15 as a light source and the inside of the subject 900 as an object to be imaged can be increased. As a result, the optical distance between the illuminating unit 15 and the inside of the subject 900 can be increased, so that the optical axes and distributions of light in different wavelength bands output from the illuminating unit 15 can be made approximately further match.

Figure 9A:
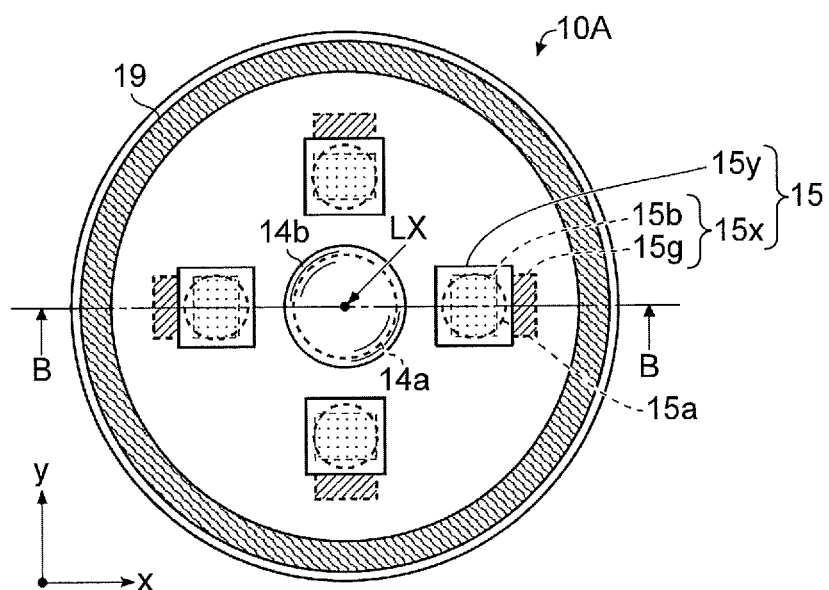
FIG. 9A is a diagram illustrating a configuration example of a capsule medical device according to a modification of the first embodiment of the invention.
Figure 9B:
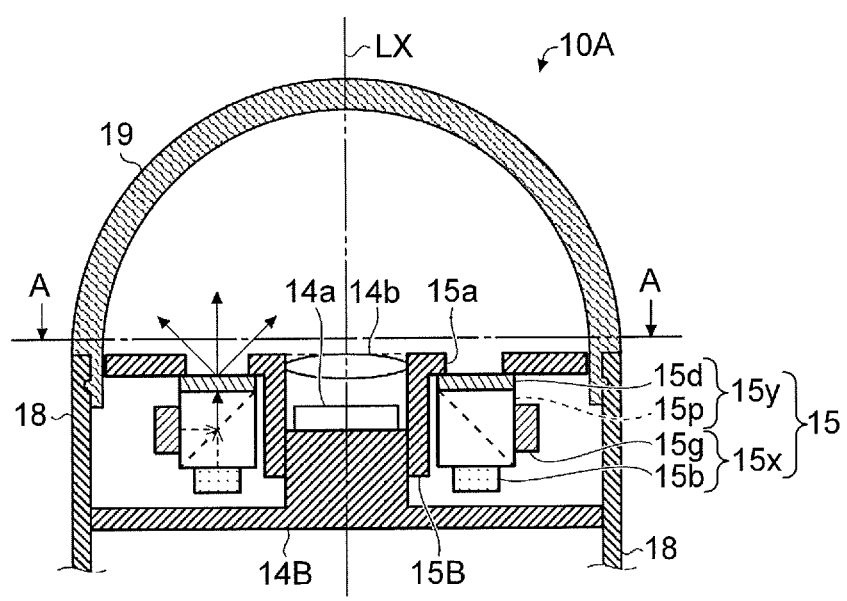
FIG. 9B is a cross section taken along line B-B in FIG. 9A.

FIGS. 9A and 9B correspond to FIGS. 5A and 5B, respectively. Since the other configuration is similar to that of the capsule medical device 10 according to the first embodiment, the detailed description will not be repeated.

Second Embodiment

Next, a capsule medical device 20 according to a second embodiment of the invention will be described in detail with reference to the drawings. In the following, for simplification of explanation, configurations similar to those of the first embodiment are denoted by the same reference numerals and their detailed description will not be repeated. In the second embodiment, the case of applying the capsule medical device 20 as a body-introducable apparatus floating in the liquid 904 accumulated in the stomach 902 will be described as an example, in a manner similar to the first embodiment of the invention. The invention, however, is not limited to the case but the capsule medical device 20 according to the embodiment can be applied to a body-introducable apparatus of acquiring an image of the inside of the subject 900 during travel from the esophagus to the anus.

Figure 10A:
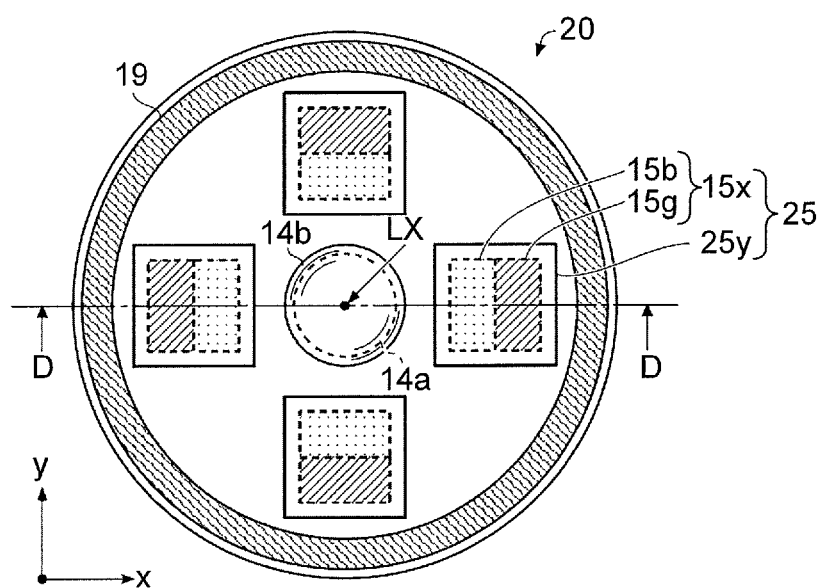
FIG. 10A is a diagram illustrating a configuration example of a capsule medical device according to the second embodiment of the invention.
Figure 10B:
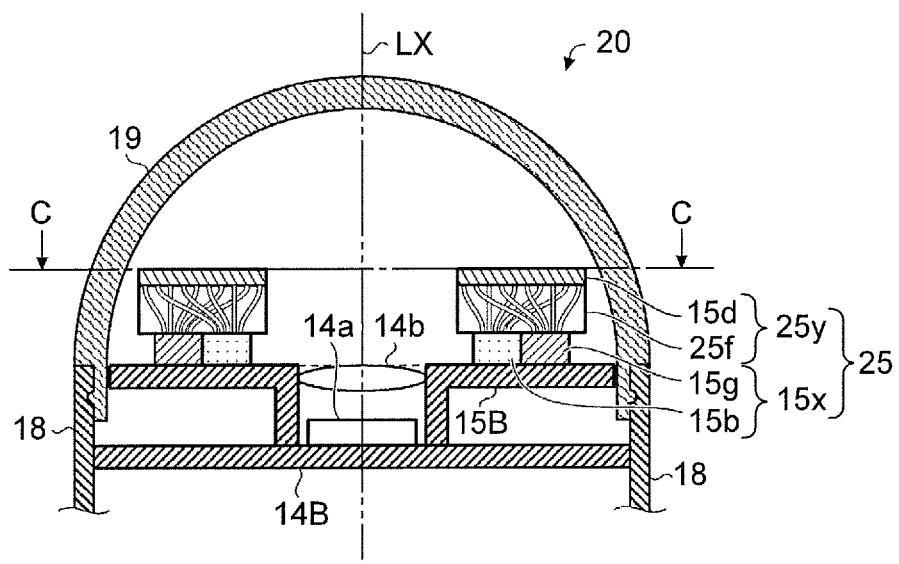
FIG. 10B is a cross section taken along line D-D in FIG. 10A.

FIGS. 10A and 10B are diagrams illustrating a configuration example of the capsule medical device 20 according to the embodiment. FIG. 10A is a cross section taken along line C-C in FIG. 10B, and FIG. 10B is a cross section taken along line D-D in FIG. 10A.

The capsule medical device 20 according to the embodiment has a configuration similar to that of the capsule medical device 10 according to the first embodiment of the invention. Obviously from comparison between FIGS. 10A and 10B and FIGS. 5A and 5B, in the capsule medical device 20 according to the embodiment, the illuminating unit 15 in the capsule medical device 10 is replaced with an illuminating unit 25.

In the illuminating unit 25, the light distribution matching unit 15y in the illuminating unit 15 illustrated in FIG. 8 is replaced with a light distribution matching unit 25y. Obviously from comparison between the light distribution matching unit 15y (refer to, for example, FIG. 5B) and the light distribution matching unit 25y (refer to, for example, FIG. 10B), in the light distribution matching unit 25y, the dichroic prism 15p in the light distribution matching unit 15y is replaced with a fiber group 25f formed by bundling a plurality of fibers. In the illuminating unit 25, the two LEDs 15b and 15g outputting the first and second special light L15b and L15g are disposed under the fiber group 25f.

Light input ends of the fibers in the fiber group 25f are aligned on the side where the LEDs 15b and 15g are disposed. On the other hand, light output ends of the fibers are aligned on the side of the top face where the diffuser 15d is disposed. The fibers are crossed so that the first special light L15b incident from the LED 15b and the second special light L15g incident from the LED 15g is output uniformly from the entire light outgoing face of the fiber group 25f. Therefore, each of the first and second special light L15b and L15g incident on the fiber group 25f passes through each of the fibers, is dispersed, and goes out from the light outgoing face of the fiber group 25f. After that, the light is incident and diffused by the diffuser 15d and goes out from the light outgoing face as the top face of the diffuser 15d.

With such a configuration, the first and second special light L15b and L15g output from the LEDs 15b and 15g is dispersed and output almost uniformly from the entire light outgoing face of the fiber group 25f. By the dispersion, the first special light L15b and the second special light L15g whose optical axes and distributions are matched can be diffused by the diffuser 15d. Consequently, in a manner similar to the first embodiment of the invention, light in different wavelength bands (the first and second special light) whose optical axes and distributions are matched can be output from each of the illuminating units 25. In the capsule medical device 20 in the embodiment, in a manner similar to the capsule medical device 10 according to the first embodiment of the invention, the plurality of illuminating units 25 are arranged (refer to, for example, FIG. 10A) point-symmetrically using one point on the optical axis LX of the objective lens 14c as a center or line-symmetrically using a straight line passing through one point on the optical axis LX as a center line. Consequently, in the case of simultaneously driving the plurality of illuminating units 25, the optical axes and distributions of the entire light in the different wavelength bands output from the entire illuminating units 25 to the image capturing direction can be made matched.

By illuminating the inside of the subject 900 with light in different wavelength bands and whose optical axes and distributions are matched as described above, in a manner similar to the first embodiment of the invention, the brightness distributions of image data of color components obtained by the imaging unit 14 can be made coincide. As a result, image data of an in-vivo image of the subject with reduced color unevenness can be generated.

Further, in the embodiment, the cap 19 as an optical window of the capsule medical device 20 has the optical function of adjusting the distribution of light passing through the cap 19. Therefore, the optical axes and distributions of light in different wavelength bands can be further matched.

Since the other configurations and effects are similar to those of the first embodiment, their detailed description will not be given here.

Like the capsule medical device 10A as the first modification of the first embodiment of the invention, the capsule medical device 20 according to the second embodiment may have a configuration that the illuminating unit 25 is disposed on the face opposite from the cap 19 of the circuit board 15B. Since such a specific configuration can be easily reached from FIGS. 9A and 9B, the detailed description will not be given here.

Third Embodiment

Next, a capsule medical device 30 according to a third embodiment of the invention will be described in detail with reference to the drawings. In the following, for simplification of explanation, configurations similar to those of the first or second embodiment are denoted by the same reference numerals and their detailed description will not be repeated. In the third embodiment, in a manner similar to the first embodiment of the invention, the case of applying the capsule medical device 30 as a body-introducable apparatus floating in the liquid 904 accumulated in the stomach 902 will be described as an example. The invention, however, is not limited to the case but the capsule medical device 30 according to the embodiment can be applied to a body-introducable apparatus of acquiring an image of the inside of the subject 900 during travel from the esophagus to the anus.

Figure 11A:
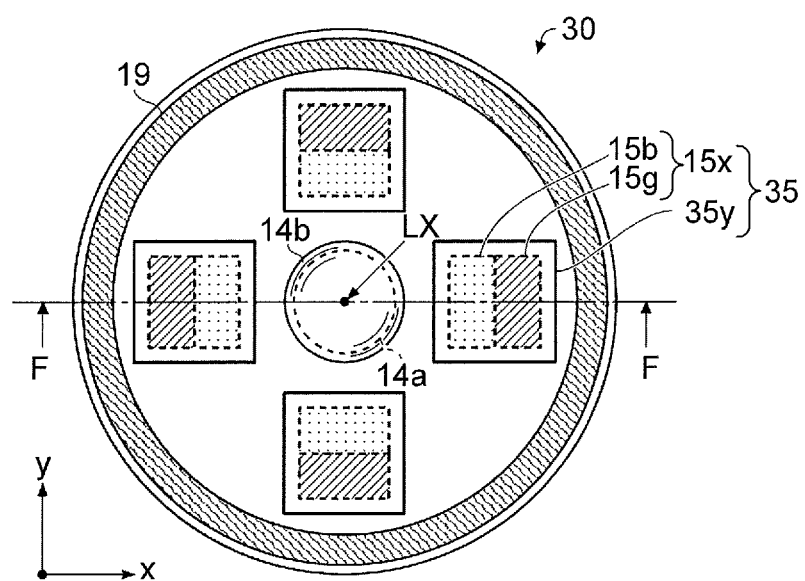
FIG. 11A is a diagram illustrating a configuration example of a capsule medical device according to the third embodiment of the invention.
Figure 11B:
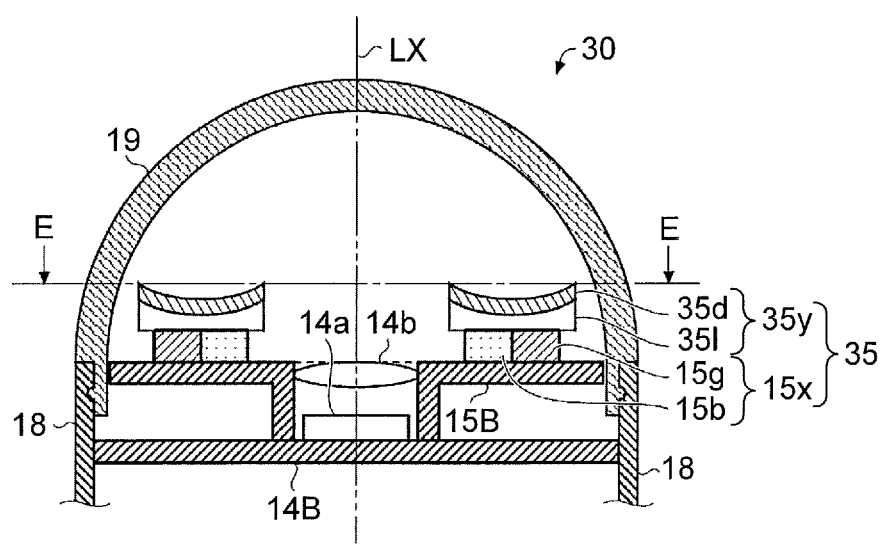
FIG. 11B is a cross section taken along line F-F in FIG. 11A.

FIGS. 11A and 11B are diagrams illustrating a configuration example of the capsule medical device 30 according to the embodiment. FIG. 11A is a cross section taken along line E-E in FIG. 11B, and FIG. 11B is a cross section taken along line F-F in FIG. 11A.

The capsule medical device 30 according to the embodiment has a configuration similar to that of the capsule medical device 10 according to the first embodiment of the invention. Obviously from comparison between FIGS. 11A and 11B and FIGS. 5A and 5B, in the capsule medical device 30 according to the embodiment, the illuminating unit 15 in the capsule medical device 10 is replaced with an illuminating unit 35.

In the illuminating unit 35, the light distribution matching unit 15y in the illuminating unit 15 illustrated in FIG. 8 is replaced with a light distribution matching unit 35y. Obviously from comparison between the light distribution matching unit 15y (refer to, for example, FIG. 5B) and the light distribution matching unit 35y (refer to, for example, FIG. 11B), in the light distribution matching unit 35y, the dichroic prism 15p in the light distribution matching unit 15y is replaced with a plano-concave lens 351, and the diffuser 15d having a plate shape is replaced with a diffuser 35d curved along the concave face of the plano-concave lens 351. In the illuminating unit 35, the two LEDs 15b and 15g outputting the first and second special light L15b and L15g are disposed under the plano-concave lens 351.

The light incident face of the plano-concave lens 351 is a flat face on which the LEDs 15b and 15g are disposed. The light incident face is set as the under face. On the other hand, the light outgoing face of the plano-concave lens 351 is a concave face on which the diffuser 35d is disposed. The light outgoing face is set as the top face. By disposing the plano-concave lens 351 in such a manner, the first and second special light L15b and L15g incident on the light incident face as a flat face is diffused by the light outgoing face as a concave face and goes out. Therefore, the optical distance between the LEDs 15b and 15g and the inner wall of the subject 900 as an object to be imaged can be increased. As a result, the optical axes and distributions of the first and second special light L15b and L15g output from the illuminating units 15 can be approximately matched. The first and second special light L15b and L15g whose optical axes and distributions are approximately matched is incident and diffused by the diffuser 35d disposed on the light outgoing face and, after that, output from the light outgoing face as the top face of the diffuser 35d.

With such a configuration, the first and second special light L15b and L15g output from the LEDs 15b and 15g is diffused by the plano-concave lens 351, and the first special light L15b and the second special light L15g whose optical axes and distributions are matched by the diffusion can be further diffused by the diffuser 35d. Consequently, in a manner similar to the first embodiment of the invention, light in different wavelength bands (the first and second special light) whose optical axes and distributions are matched can be output from each of the illuminating units 35. In the capsule medical device 30 in the embodiment, in a manner similar to the capsule medical device 10 according to the first embodiment of the invention, in the case of simultaneously driving the plurality of illuminating units 35 arranged point-symmetrically using one point on the optical axis LX of the objective lens 14c as a center or line-symmetrically using a straight line passing through one point on the optical axis LX as a center line, the optical axes and distributions of the entire light in the different wavelength bands emitted from the entire illuminating units 35 to the image capturing direction can be made matched.

By illuminating the inside of the subject 900 with light in different wavelength bands and whose optical axes and distributions are matched as described above, in a manner similar to the first embodiment of the invention, the brightness distributions of image data of color components obtained by the imaging unit 14 can be made coincide. As a result, image data of an in-vivo image of the subject with reduced color unevenness can be generated.

Further, in the embodiment, the cap 19 as an optical window of the capsule medical device 30 has the optical function of adjusting the distribution of light passing through the cap 19. Therefore, the optical axes and distributions of light in different wavelength bands can be further matched.

Since the other configurations and effects are similar to those of the first embodiment, their detailed description will not be given here.

Like the capsule medical device 10A as the first modification of the first embodiment of the invention, the capsule medical device 30 according to the third embodiment may have a configuration that the illuminating unit 35 is disposed on the face of the circuit board 15B which is opposite from the cap 19. Since such a specific configuration can be easily reached from FIGS. 9A and 9B, the detailed description will not be given here.

Fourth Embodiment

Next, a capsule medical device 40 according to a fourth embodiment of the invention will be described in detail with reference to the drawings. In the following, for simplification of explanation, configurations similar to those of any of the first to third embodiments of the invention are denoted by the same reference numerals and their detailed description will not be repeated. In the fourth embodiment, in a manner similar to the first embodiment of the invention, the case of applying the capsule medical device 40 as a body-introducable apparatus floating in the liquid 904 accumulated in the stomach 902 will be described as an example. The invention, however, is not limited to the case but the capsule medical device 40 according to the embodiment can be applied to a body-introducable apparatus of acquiring an image of the inside of the subject 900 during travel from the esophagus to the anus.

Figure 12A:
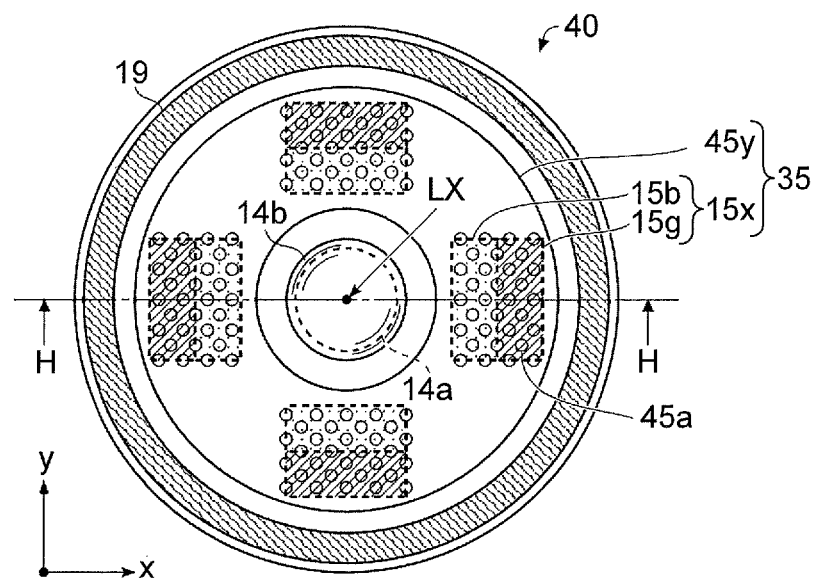
FIG. 12A is a diagram illustrating a configuration example of a capsule medical device according to the fourth embodiment of the invention.
Figure 12B:
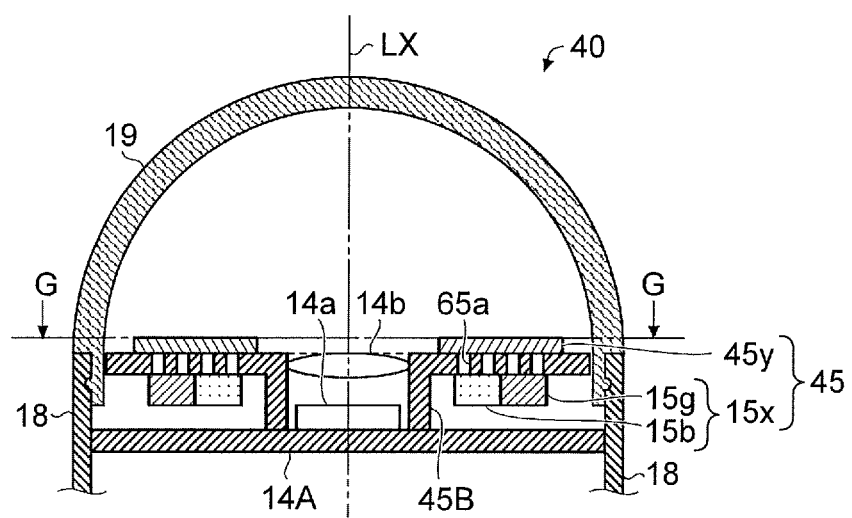
FIG. 12B is a cross section taken along line H-H in FIG. 12A.

FIGS. 12A and 12B are diagrams illustrating a configuration example of the capsule medical device 40 according to the fourth embodiment. FIG. 12A is a cross section taken along line G-G in FIG. 12B, and FIG. 12B is a cross section taken along line H-H in FIG. 12A.

The capsule medical device 40 according to the embodiment has a configuration similar to that of the capsule medical device 10 according to the first embodiment of the invention. Obviously from comparison between FIGS. 12A and 12B and FIGS. 5A and 5B, in the capsule medical device 40 according to the embodiment, the illuminating unit 15 in the capsule medical device 10 is replaced with an illuminating unit 45, and the circuit board 15B on which the illuminating control circuit 15A is mounted is replaced with a circuit board 45B.

In the illuminating unit 45, the light distribution matching unit 15y in the illuminating unit 15 illustrated in FIG. 8 is replaced with a light distribution matching unit 45y, and the light source 15x including the two LEDs 15b and 15g outputting the first and second special light L15b and L15g is disposed on the face (which will be called a rear face) opposite from the cap 19 of the circuit board 45B.

The light distribution matching unit 45y is a ring-shaped diffuser covering almost the entire face on the cap 19 side of the circuit board 45B. Specifically, in the embodiment, the common light distribution matching unit 45y is used for the plurality of illuminating units 45. The light distribution matching unit 45y has a point-symmetrical shape using one point on the optical axis LX of the objective lens 14c as a center or a line-symmetrical shape using a straight line passing one point on the optical axis LX as a center line. A hole formed in the center of the light distribution matching unit 45y is a window for making light entering through the cap 19 directly incident on the imaging element 15a.

In the circuit board 45B, an opening 45a for passing, to the cap 19 side, the first and second special light L15b and L15g output from the light source 15x (the LEDs 15b and 15g) disposed on the face opposite from the cap 19 side is formed. Therefore, the first and second special light L15b and L15g output from the LEDs 15b and 15g is incident on the light distribution matching unit 45y via the opening 45a, diffused by the light distribution matching unit 45y, and output from the light outgoing face as the top face of the light distribution matching unit 45y.

With such a configuration, the first and second special light L15b and L15g output from the LEDs 15b and 15g can be diffused by the ring-shaped light distribution matching unit 45y. Consequently, in a manner similar to the first embodiment of the invention, light in different wavelength bands (the first and second special light) whose optical axes and distributions are matched can be output from each of the illuminating units 45. In the capsule medical device 40 in the embodiment, in a manner similar to the capsule medical device 10 according to the first embodiment of the invention, the plurality of illuminating units 45 are arranged point-symmetrically using one point on the optical axis LX of the objective lens 14c as a center or line-symmetrically using a straight line passing through one point on the optical axis LX as a center line (refer to, for example, FIG. 12A). Therefore, in the case of simultaneously driving the plurality of illuminating units 45, the optical axes and distributions of the entire light in the different wavelength bands emitted from the entire illuminating units 45 to the image capturing direction can be made matched.

By illuminating the inside of the subject 900 with light in different wavelength bands and whose optical axes and distributions are matched as described above, in a manner similar to the first embodiment of the invention, the brightness distributions of image data of color components obtained by the imaging unit 14 can be made coincide. As a result, image data of an in-vivo image of the subject with reduced color unevenness can be generated.

Further, in the embodiment, the cap 19 as an optical window of the capsule medical device 40 has the optical function of adjusting the distribution of light passing through the cap 19. Therefore, the optical axes and distributions of light in different wavelength bands can be further matched.

Since the other configurations and effects are similar to those of the first embodiment, their detailed description will not be given here.

Fifth Embodiment

Next, a capsule medical device 50 according to a fifth embodiment of the invention will be described in detail with reference to the drawings. In the following, for simplification of explanation, configurations similar to those of any of the first to fourth embodiments of the invention are denoted by the same reference numerals and their detailed description will not be repeated. In the fifth embodiment, in a manner similar to the first embodiment of the invention, the case of applying the capsule medical device 50 as a body-introducable apparatus floating in the liquid 904 accumulated in the stomach 902 will be described as an example. The invention, however, is not limited to the case but the capsule medical device 50 according to the embodiment can be applied to a body-introducable apparatus of acquiring an image of the inside of the subject 900 during travel from the esophagus to the anus.

Figure 13A:
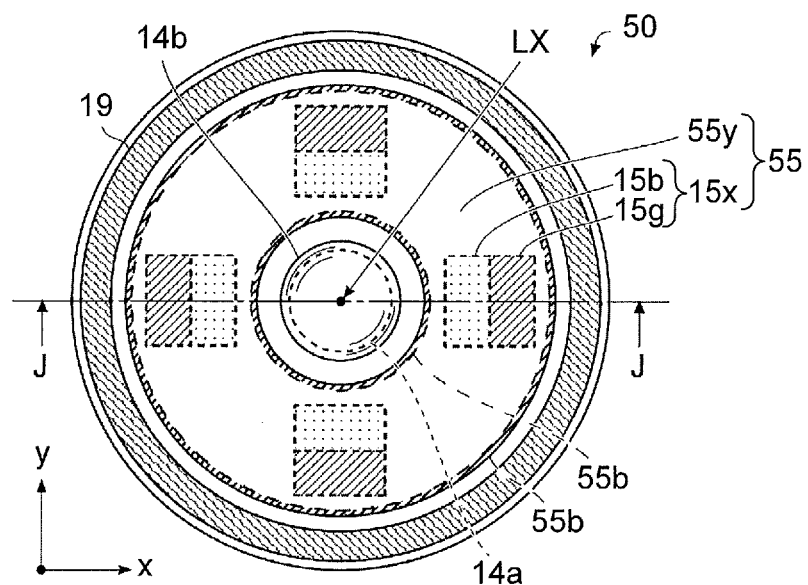
FIG. 13A is a diagram illustrating a configuration example of a capsule medical device according to the fifth embodiment of the invention.
Figure 13B:
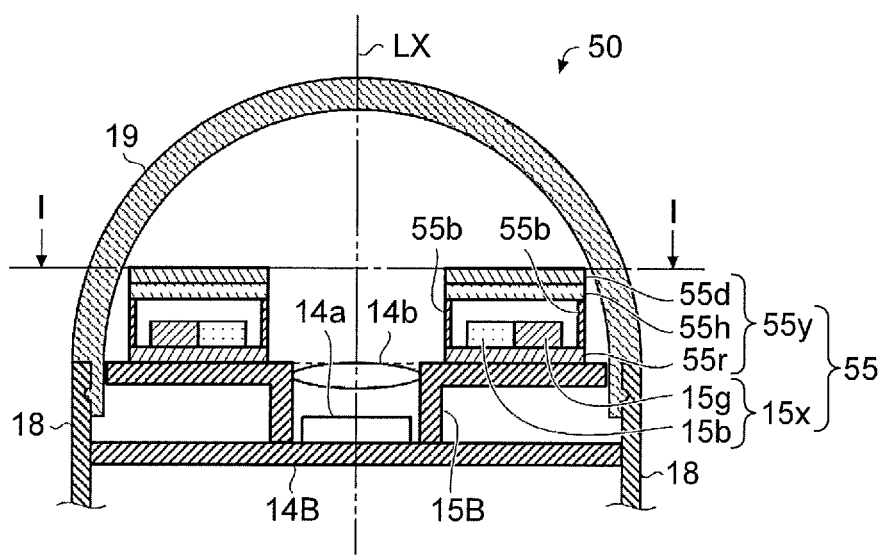
FIG. 13B is a cross section taken along line J-J in FIG. 13A.

FIGS. 13A and 13B are diagrams illustrating a configuration example of the capsule medical device 50 according to the fourth embodiment. FIG. 13A is a cross section taken along line I-I in FIG. 13B, and FIG. 13B is a cross section taken along line J-J in FIG. 13A.

The capsule medical device 50 according to the embodiment has a configuration similar to that of the capsule medical device 10 according to the first embodiment of the invention. Obviously from comparison between FIGS. 13A and 13B and FIGS. 5A and 5B, in the capsule medical device 50 according to the embodiment, the illuminating unit 15 in the capsule medical device 10 is replaced with an illuminating unit 55.

In the illuminating unit 55, the light distribution matching unit 15y in the illuminating unit 15 illustrated in FIG. 8 is replaced with a light distribution matching unit 55y. Obviously from comparison between the light distribution matching unit 15y (refer to, for example, FIG. 5B) and the light distribution matching unit 55y (refer to, for example, FIG. 13B), in the light distribution matching unit 55y, the dichroic prism 15p in the light distribution matching unit 15y is replaced with a reflection region, which is formed of a mirror 55r on the lower side and a half mirror 55h on the upper side, and the diffuser 15d is replaced with a ring-shaped diffuser 55d similar to the diffuser 35d in the fourth embodiment of the invention. In the illuminating unit 55, the two LEDs 15b and 15g outputting the first and second special light L15b and L15g are disposed in a region sandwiched between the mirror 55r and the half mirror 55h. The side wall of the region sandwiched by the mirror 55r and the half mirror 55h is formed by, for example, a mirror 55b whose inner face is a mirror face.

Each of the mirror 55r and the half mirror 55h is a ring-shaped member covering almost the entire face on the cap 19 side of the circuit board 15. The mirror 55r totally reflects the first and second special light L15b and L15g output from the light source 15x. On the other hand, the half mirror 55h reflects, for example, about 50% of the first and second special light L15b and L15g output from the light source 15x and transmits about 50% of the light. Therefore, each of the first and second special light L15b and L15g output from the LEDs 15b and 15g is diffused by being repetitively reflected in the reflection region formed by the mirror 55r and the half mirror 55h disposed apart from each other. Then, the light is incident and further diffused in the diffuser 55d disposed on the top face of the half mirror 55h as the light outgoing face of the reflection region. After that, the light goes out from the light outgoing face as the top face of the diffuser 55d.

With such a configuration, the first and second special light L15b and L15g output from the LEDs 15b and 15g can be diffused in the ring-shaped reflection region formed of the mirror 55r and the half mirror 55h, and the first and second special light L15b and L15g whose optical axes and distributions are matched by the diffusion can be further diffused by the diffuser 55d. Consequently, in a manner similar to the first embodiment of the invention, light in different wavelength bands and whose optical axes and distributions are matched can be output from each of the illuminating units 55. In the capsule medical device 50 in the embodiment, in a manner similar to the capsule medical device 10 according to the first embodiment of the invention, the plurality of illuminating units 55 are arranged point-symmetrically using one point on the optical axis LX of the objective lens 14c as a center or line-symmetrically using a straight line passing through one point on the optical axis LX as a center line (refer to, for example, FIG. 13A). Therefore, in the case of simultaneously driving the plurality of illuminating units 55, the optical axes and distributions of the entire light in the different wavelength bands emitted from the entire illuminating units 55 to the image capturing direction can be made matched.

By illuminating the inside of the subject 900 with light in different wavelength bands and whose optical axes and distributions are matched as described above, in a manner similar to the first embodiment of the invention, the brightness distributions of image data of color components obtained by the imaging unit 14 can be made coincide. As a result, image data of an in-vivo image of the subject with reduced color unevenness can be generated.

Further, in the embodiment, the cap 19 as an optical window of the capsule medical device 50 has the optical function of adjusting the distribution of light passing through the cap 19. Therefore, the optical axes and distributions of light in different wavelength bands can be further matched.

Since the other configurations and effects are similar to those of the first embodiment, their detailed description will not be given here.

Like the capsule medical device 10A as the first modification of the first embodiment of the invention, the capsule medical device 50 according to the fifth embodiment may have a configuration that the illuminating unit 55 is disposed on the face opposite from the cap 19 of the circuit board 15B. Since such a specific configuration can be easily reached from FIGS. 9A and 9B, the detailed description will not be given here.

Sixth Embodiment

Next, a capsule medical device 60 according to a sixth embodiment of the invention will be described in detail with reference to the drawings. In the following, for simplification of explanation, configurations similar to those of any of the first to fifth embodiments of the invention are denoted by the same reference numerals and their detailed description will not be repeated. In the sixth embodiment, in a manner similar to the first embodiment of the invention, the case of applying the capsule medical device 60 as a body-introducable apparatus floating in the liquid 904 accumulated in the stomach 902 will be described as an example. The invention, however, is not limited to the case but the capsule medical device 60 according to the embodiment can be applied to a body-introducable apparatus of acquiring an image of the inside of the subject 900 during travel from the esophagus to the anus.

Figure 14A:
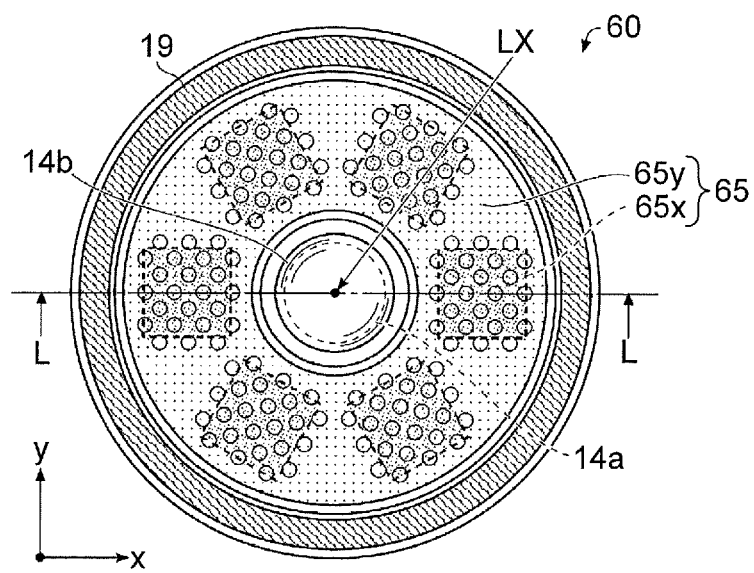
FIG. 14A is a diagram illustrating a configuration example of a capsule medical device according to the sixth embodiment of the invention.
Figure 14B:
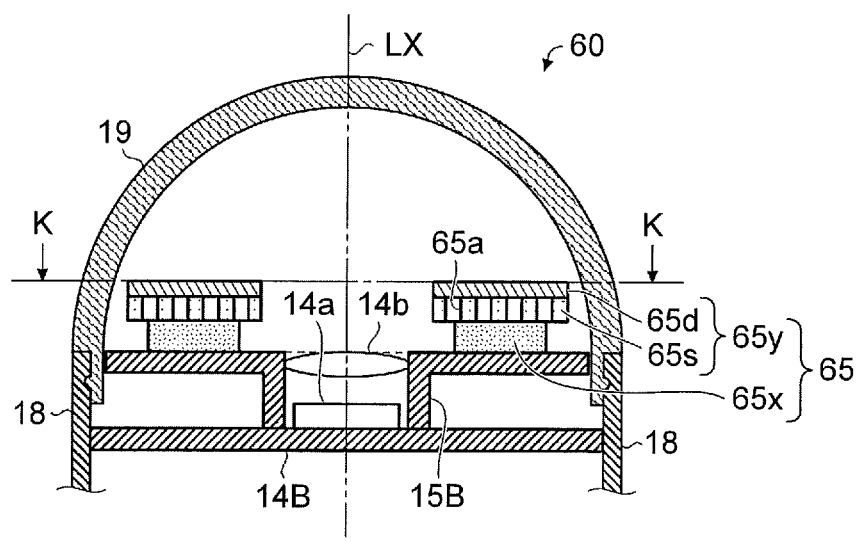
FIG. 14B is a cross section taken along line L-L in FIG. 14A.

FIGS. 14A and 14B are diagrams illustrating a configuration example of the capsule medical device 60 according to the sixth embodiment. FIG. 14A is a cross section taken along line K-K in FIG. 14B, and FIG. 14B is a cross section taken along line L-L in FIG. 14A.

The capsule medical device 60 according to the embodiment has a configuration similar to that of the capsule medical device 10 according to the first embodiment of the invention. Obviously from comparison between FIGS. 14A and 14B and FIGS. 5A and 5B, in the capsule medical device 60 according to the embodiment, the illuminating unit 15 in the capsule medical device 10 is replaced with an illuminating unit 65.

In the illuminating unit 65, the light source 15x in the illuminating unit 15 illustrated in FIG. 8 is replaced with a light source 65x, and the light distribution matching unit 15y is replaced with a light distribution matching unit 65y. The light source 65x is made by, for example, an LED that outputs the first special light L15b.

The light distribution matching unit 65y is disposed on the top face as the light outgoing face of the light source 65x. As obvious when compared with the light distribution matching unit 15y illustrated in, for example, FIG. 5B, in the light distribution matching unit 65y, the dichroic prism 15p in the light distribution matching unit 15y is replaced with a wavelength shifter 65s having a ring-plate shape covering almost the entire face on the cap 19 side of the circuit board 15 and converting the first special light L15b in the wavelength band $W_{15b}$ around 415 nm to the second special light L15g in the wavelength band $W_{15g}$ around 540 nm. The diffuser 15d is replaced with a diffuser 65d similar to the diffuser 35d in the fourth embodiment.

The wavelength shifter 65s includes a phosphor which absorbs and excites the first special light in the wavelength band $W_{15b}$ around 415 nm and, after that, at the time of returning to the ground state, releasing the second special light in the wavelength band $W_{15g}$ around 540 nm.

In a region positioned above the light sources 65x in the wavelength shifter 65s, a plurality of through holes 65a are formed. The total opening area of the plurality of through holes 65a occupies about the half of the region above the light sources 65x. The through hole 65a is a hole for making the first special light L15b output from the light source 65x directly incident on the diffuser 65d. The through holes 65a are formed dispersedly so that the first special light L15b is uniformly output from the entire region above the light source 65x. Therefore, on the diffuser 65d, the first special light L15b output from the light source 65x and the second special light L15g whose wavelength band is converted by passing through the wavelength shifter 65s is dispersedly incident with almost the same light amounts. The light incident on the diffuser 65d is diffused by the diffuser 65d and, after that, output from the light outgoing face as the top face of the diffuser 65d.

With such a configuration, the first special light L15b output from the light source 65x and the second special light L15g generated by converting the wavelength of the first special light L15b can be dispersedly output and the first and second special light L15b and L15g whose optical axes and distributions are almost matched by the diffusion can be diffused by the diffuser 65d. Consequently, in a manner similar to the first embodiment of the invention, light in different wavelength bands and whose optical axes and distributions (the first and second special light) are matched can be output from the entire illuminating units 65. In the capsule medical device 60 in the embodiment, in a manner similar to the capsule medical device 10 according to the first embodiment of the invention, the plurality of illuminating units 65 are arranged point-symmetrically using one point on the optical axis LX of the objective lens 14c as a center or line-symmetrically using a straight line passing through one point on the optical axis LX as a center line (refer to, for example, FIG. 14A). Therefore, in the case of simultaneously driving the plurality of illuminating units 65, the optical axes and distributions of the entire light in the different wavelength bands emitted from the plurality of illuminating units 65 to the image capturing direction can be made matched.

By illuminating the inside of the subject 900 with light in different wavelength bands and whose optical axes and distributions are matched as described above, in a manner similar to the first embodiment of the invention, the brightness distributions of image data of color components obtained by the imaging unit 14 can be made coincide. As a result, image data of an in-vivo image of the subject with reduced color unevenness can be generated.

Further, in the embodiment, the cap 19 as an optical window of the capsule medical device 60 has the optical function of adjusting the distribution of light passing through the cap 19. Therefore, the optical axes and distributions of light in different wavelength bands can be further matched.

Since the other configurations and effects are similar to those of the first embodiment, their detailed description will not be given here.

Like the capsule medical device 10A as the first modification of the first embodiment of the invention, the capsule medical device 60 according to the sixth embodiment may have a configuration that the illuminating unit 65 is disposed on the face opposite to the cap 19 of the circuit board 15B. Since such a specific configuration can be easily reached from FIGS. 9A and 9B, the detailed description will not be given here.

First Modification

In the embodiment, the wavelength shifter 65s having the through holes 65a is used as means for converting a part of the first special light L15b output from the light source 65x to the second special light L15g having a wavelength longer than that of the first special light L15b by using, as the light source 65x, the LED that outputs the first special light L15b. The invention, however, is not limited to the configuration. For example, as illustrated in a capsule medical device 60A according to a first modification of the sixth embodiment in FIGS. 15A and 15B, a white LED that outputs white light may be used as a light source 65x-1, and the first and second special light L15b and L15g may be generated from the light source 65x-1. In this case, as the configuration of converting white light to the first and second special light L15b and L15g, for example, an optical filter obtained by combining a filter 65b (first filter) passing light in the wavelength band around 415 nm (first special light) in the white light and a filter 65g (second filter) passing light in the wavelength band around 540 nm (second special light) can be used.

Therefore, an illuminating unit 65-1 of the modification has a configuration that the light source 65x-1 has the white LED (white light source), and a light distribution matching unit 65y-1 has the optical filter made by the filters 65b and 65g and the diffuser 65d. The optical filter has a configuration that, for example, the wavelength shifter 65s in the foregoing embodiment is replaced with the filter 65b and the through hole 65a in the wavelength shifter 65s is replaced with the filter 65g.

Figure 15A:
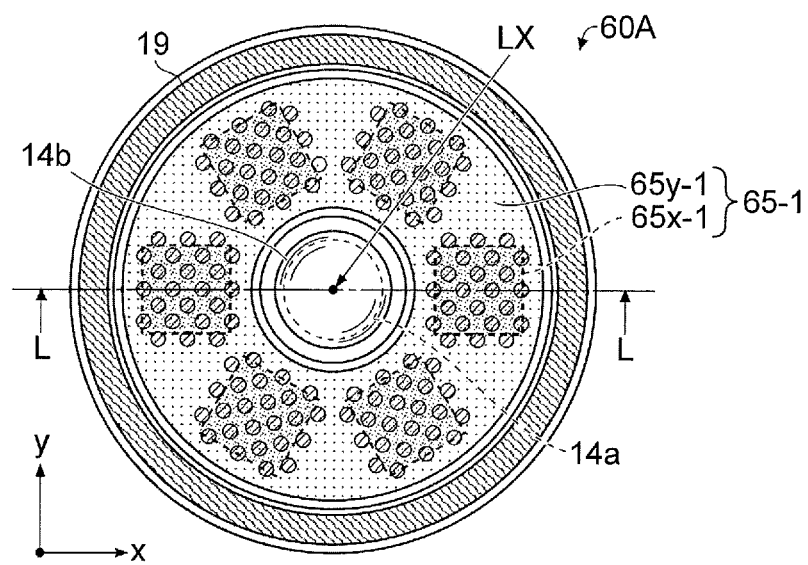
FIG. 15A is a diagram illustrating a configuration example of a capsule medical device according to a modification of the sixth embodiment of the invention.
Figure 15B:
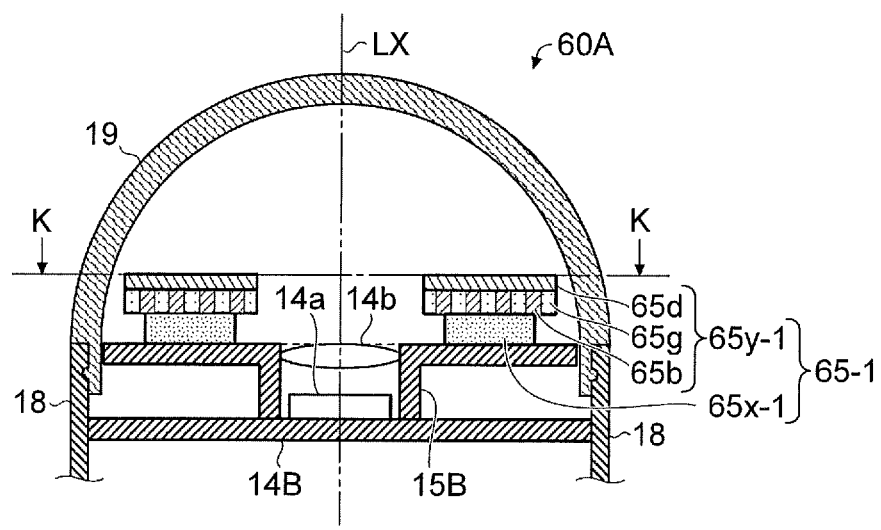
FIG. 15B is a cross section taken along line L-L in FIG. 15A.

FIGS. 15A and 15B correspond to FIGS. 5A and 5B, respectively. Since the other configuration is similar to that of the capsule medical device 60 according to the sixth embodiment, the detailed description will not be repeated.

Seventh Embodiment

Next, a capsule medical device 70 according to a seventh embodiment of the invention will be described in detail with reference to the drawings. In the following, for simplification of explanation configurations similar to those of any of the first to sixth embodiments of the invention are denoted by the same reference numerals and their detailed description will not be repeated. In the seventh embodiment, in a manner similar to the first embodiment of the invention, the case of applying the capsule medical device 70 as a body-introducable apparatus floating in the liquid 904 accumulated in the stomach 902 will be described as an example. The invention, however, is not limited to the case but the capsule medical device 70 according to the embodiment can be applied to a body-introducable apparatus of acquiring an image of the inside of the subject 900 during travel from the esophagus to the anus.

The capsule medical device 70 according to the seventh embodiment can execute simultaneously or individually special light observation of capturing an image while illuminating the inside of the subject 900 with special light and normal light observation of capturing an image while illuminating the inside of the subject 900 with normal light.

Figure 16:
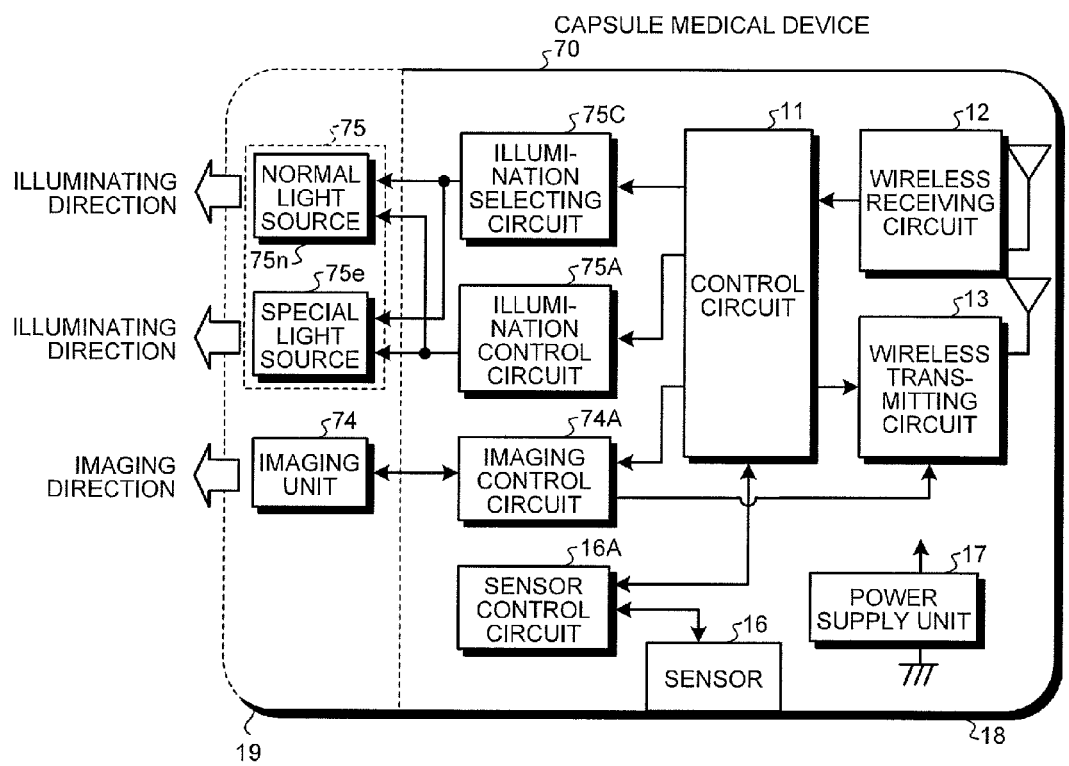
FIG. 16 is a block diagram illustrating a schematic configuration of a capsule medical device in a medical system according to the seventh embodiment of the invention.

FIG. 16 is a schematic block diagram of the capsule medical device 70 according to the seventh embodiment.

As illustrated in FIG. 16, the capsule medical device 70 has: an imaging unit 74 for capturing an image of the inside of the subject 900; an imaging control circuit 74A for acquiring image data by driving the imaging unit 74; a plurality of illuminating units 75 each for outputting one or more kinds of special light and/or normal light; an illumination control circuit 75A for illuminating the imaging direction by driving the illuminating units 75 at the time of capturing an image of the inside of the subject 900 by the imaging unit 74; and an illumination selecting circuit 75C for selecting at least one of a special light source 75e and a normal light source 75n as an illuminating unit driven at the time of imaging. The illuminating unit 75 includes the special light source 75e that outputs special light of one or more kinds, and the normal light source 75n that outputs normal light. The other configuration is similar to that of the capsule medical device 10 according to the first embodiment of the invention.

Imaging Unit and Illuminating Unit

Figure 17:
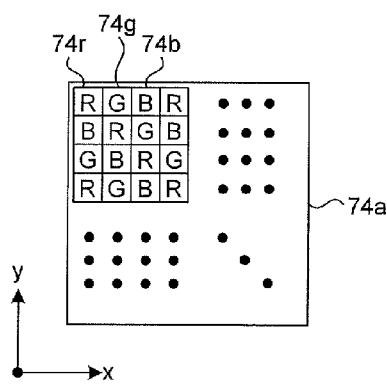
FIG. 17 is a conceptual diagram illustrating an example of an array of imaging elements in an imaging unit in the capsule medical device according to the seventh embodiment of the invention.
Figure 18A:
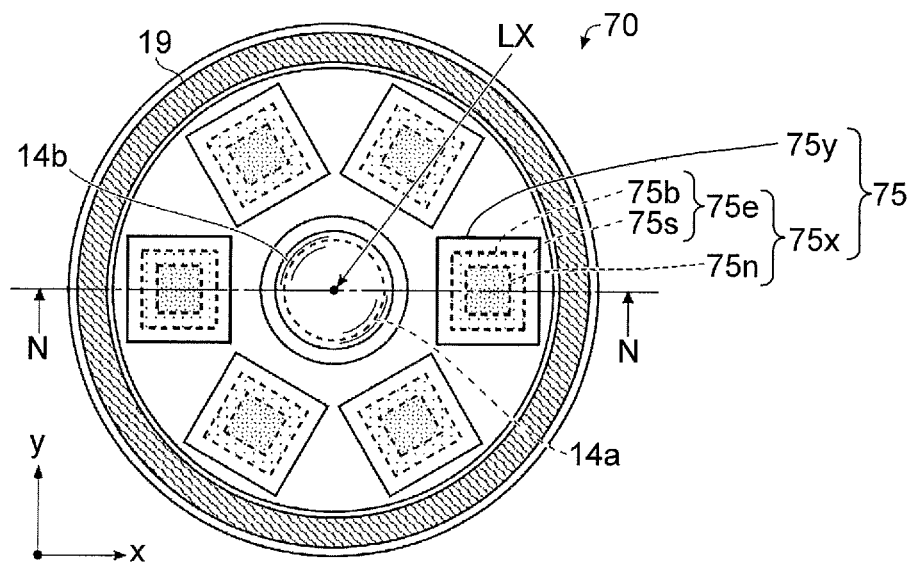
FIG. 18A is a diagram illustrating a configuration example of the capsule medical device according to the seventh embodiment of the invention.
Figure 18B:
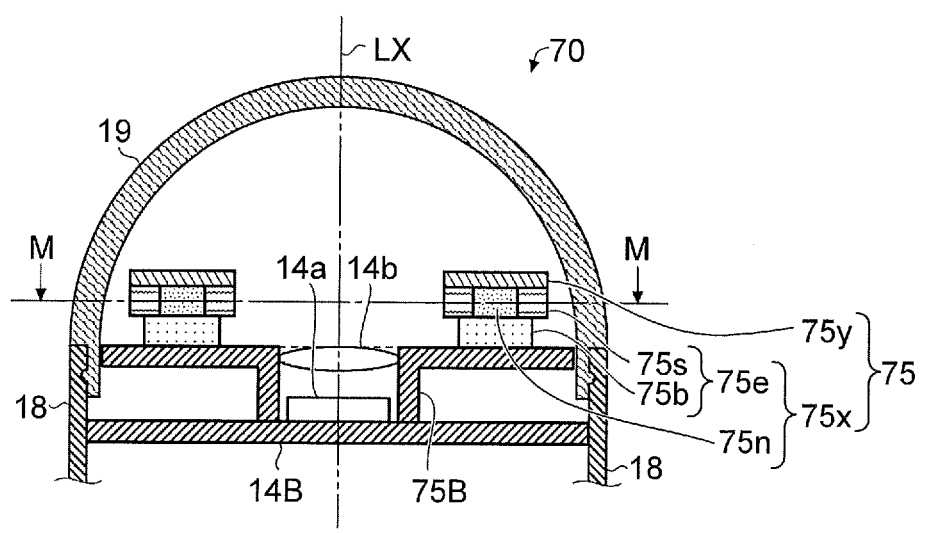
FIG. 18B is a cross section taken along line N-N in FIG. 18A.

A more-detailed configuration example of the imaging unit 74 and the illuminating unit 75 in the capsule medical device 70 according to the embodiment will be described specifically by using the drawings. FIG. 17 is a layout diagram illustrating an example of an array of the imaging elements 74a in the imaging unit 74 according to the embodiment. FIGS. 18A and 18B are diagrams illustrating a configuration example of the capsule medical device 70 according to the embodiment. FIG. 18A is a cross section taken along line M-M in FIG. 18B, and FIG. 18B is a cross section taken along line N-N in FIG. 18A.

Imaging Unit

In the imaging unit 74 of the embodiment, in the configuration illustrated in FIG. 3, the imaging element 14a is replaced with an imaging element 74a. The imaging element 74a has, as illustrated in FIG. 17, a CCD or CMOS structure in which a plurality of light receiving elements 74r, a plurality of light receiving elements 74g, and a plurality of light receiving elements 74b are arranged in order in row and column directions (x and y directions in the diagram). The light receiving elements 74g and 74g are similar to the light receiving elements 14g and 14b, respectively, in the first embodiment of the invention. The light receiving element 74r has, for example, a light reception sensitivity band having a peak around 700 nm. Therefore, the imaging element 74a generates image data of a red component (R), image data of a green component (G), and image data of a blue component (B).

Illuminating Unit

Each of the illuminating units 75 according to the embodiment includes a light source made by a plurality of Light Emitting Diodes (LEDs) outputting a plurality of kinds of special light and normal light. The illuminating unit 75 is mounted on a circuit board 75B having the illuminating control circuit 75A for controlling the light source, and the illumination selecting circuit 75C for selecting a light source to be driven from the light sources. For example, the illuminating control circuit 75A drives the illuminating unit 15 to illuminate the inside of the subject 900 synchronously with an image capturing timing under control of the control circuit 11. The illumination selecting circuit 75C selects, for example, a light source to be driven at the time of imaging under control of the control circuit 11.

As illustrated in FIGS. 18A and 18B, each of the illuminating units 75 has a light source 75x for properly outputting first and second special light and normal light, and a light distribution matching unit 75y for adjusting distribution of the various light output from the light source 75x. The light source 75x includes a special light source 75e outputting the first and second special light and a normal light source 75n (white light source) outputting the normal light.

The special light source 75e has an LED 75b outputting the first special light and a wavelength shifter 75s provided on the light outgoing face (top face) of the LED 75b. In the wavelength shifter 75s, an opening for exposing a part of the LED 75b is formed. The center of the opening coincides with the optical axis of the LED 75b. The area of the opening is, for example, almost the half of the area of the light outgoing face of the LED 75b. Further, the opening is provided with a normal light source 75n.

The normal light source 75n includes an LED having a transparent resin and a light emitting electrode, and outputs normal light. The optical axis of the normal light source 75n coincides with that of the LED 75b in the special light source 75e.

Therefore, in the case of driving only the special light source 75e, the light source 75x outputs first special light which is passed through a transparent part in the normal light source 75n, and second special light generated by converting the wavelength of light incident on the wavelength shifter 75s. On the other hand, in the case of driving the normal light source 75n, the normal light is output from the light source 75x.

On the light outgoing face (top face) of the light source 75x, a diffuser 75d similar to the diffuser 15d in the first embodiment of the invention is disposed. Therefore, the first and second special light and/or normal light output from the light source 75x is diffused by the diffuser 75d and is output from the light outgoing face (top face) of the diffuser 75d in a state where distribution is adjusted.

As described above, in the embodiment, also in the case of simultaneously performing the special-light observation and the normal-light observation, one or more special light and normal light output from each of the light sources whose optical axes coincide can be diffused to make the distributions match. In the capsule medical device 70 according to the embodiment, in a manner similar to the capsule medical device 10 according to the first embodiment of the invention, the plurality of illuminating units 75 are arranged (refer to, for example, FIG. 18A) point-symmetrically using one point on the optical axis LX of the objective lens 14c as a center or line-symmetrically using a straight line passing through one point on the optical axis LX as a center line. Consequently, in the case of simultaneously driving the illuminating units 75, the optical axes and distributions of the entire light emitted from the entire illuminating units 75 to the image capturing direction can be made matched.

By illuminating the inside of the subject 900 with one or more special light and the normal light whose optical axes and distributions are matched as described above, the brightness distributions of image data of color components obtained by the imaging unit 74 can be made coincide. As a result, image data of an in-vivo image of the subject with reduced color unevenness can be generated.

Further, in the embodiment, the cap 19 as an optical window of the capsule medical device 20 has the optical function of adjusting the distribution of light passing through the cap 19. Therefore, the optical axes and distributions of light in different wavelength bands can be further matched.

Since the other configurations and effects are similar to those of the first embodiment of the invention, their detailed description will not be given here.

Like the capsule medical device 10A as the first modification of the first embodiment of the invention, the capsule medical device 70 according to the seventh embodiment may have a configuration that the illuminating unit 75 is disposed on the face opposite to the cap 19 of the circuit board 75B. Since such a specific configuration can be easily reached from FIGS. 9A and 9B, the detailed description will not be given here.

As described above, in the foregoing embodiment, distributions of the first and second light in different wavelength bands can be matched, so that the body-introducable apparatus and the medical system capable of illuminating the inside of a subject without causing color unevenness in a captured image can be realized.

The above and other features, advantages and technical and industrial significance of this invention will be better understood by reading the following detailed description of presently preferred embodiments of the invention, when considered in connection with the accompanying drawings.

What is claimed is:

1. A body-introducable apparatus to be introduced in a subject, comprising:
    a light source unit having a first light source that outputs first light and a second light source that outputs second light in a wavelength band different from that of the first light;
    a light distribution matching unit that matches distributions of the first light and the second light;
    an illuminating control unit that drives the light source unit to illuminate the inside of the subject; and
    an imaging unit that captures an image of the inside of the subject,
    wherein:
    the light distribution matching unit includes a mirror that reflects the first and second light and a half mirror that reflects a part of the first and second light and transmits a part of the light,
    the mirror and the half mirror are disposed apart from each other so that a reflection region is formed therebetween, and
    the first and second light sources are disposed between the mirror and the half mirror.

2. The body-introducable apparatus according to claim 1, wherein the light distribution matching unit has a diffuser for diffusing the first and second light to match light distributions.

3. The body-introducable apparatus according to claim 1, comprising a plurality of the light source units and the light distribution matching units disposed point-symmetrically or line-symmetrically.

4. The body-introducable apparatus according to claim 1, further comprising:
    a circuit board on which the light source unit is mounted; and
    an optical window disposed on the side of a first face of the circuit board and transmitting light output from the light source unit to the outside,
    wherein the light source unit is mounted on a second face on the side opposite to the first face of the circuit board, and
    a through hole for passing the light output from the light source unit to the optical window is formed in the circuit board.

5. A body-introducable apparatus to be introduced in a subject, comprising:
    a light source means having a first light source that outputs first light and a second light source that outputs second light in a wavelength band different from that of the first light;
    a light distribution matching means for matching distributions of the first light and the second light;
    an illuminating control means for driving the light source unit to illuminate the inside of the subject; and
    an imaging means for capturing an image of the inside of the subject,
    wherein:
    the light distribution matching means includes a mirror that reflects the first and second light and a half mirror that reflects a part of the first and second light and transmits a part of the light,
    the mirror and the half mirror are disposed apart from each other so that a reflection region is formed therebetween, and
    the first and second light sources are disposed between the mirror and the half mirror.

6. A medical system comprising:
    a body-introducable apparatus including:
        a light source unit having a first light source that outputs first light and a second light source that outputs second light in a wavelength band different from that of the first light,
        a light distribution matching unit that matches distributions of the first light and the second light,
        an illuminating control unit that drives the light source unit to illuminate the inside of the subject, and
        an imaging unit that captures an image of the inside of the subject,
        the light distribution matching unit including a mirror that reflects the first and second light and a half mirror that reflects a part of the first and second light and transmits a part of the light, the mirror and the half mirror being disposed apart from each other so that a reflection region is formed therebetween, and the first and second light sources being disposed between the mirror and the half mirror;
    a communication device disposed on the outside of the subject; and
    a display device that displays an image by using image data,
    wherein the body-introducable apparatus has a wireless transmitting unit that transmits image data obtained by the imaging unit as a wireless signal,
    the communication device includes a wireless receiving unit that receives the image data transmitted from the wireless transmitting unit, an image signal processing unit that processes the image data received by the wireless receiving unit, and a communication device external interface unit that stores the image data processed by the image signal processing unit to a portable recording medium detachably connected to the communication device, and
    the display device includes a display device external interface unit to which the portable recording medium can be detachably connected, and a display unit that reads the image data from the portable recording medium connected to the display device external interface unit and displays the read image data.

7. A medical system comprising:
    a body-introducable apparatus including:
        light source means having a first light source that outputs first light and a second light source that outputs second light in a wavelength band different from that of the first light, light distribution matching means for matching distributions of the first light and the second light, illuminating control means for driving the light source means to illuminate the inside of the subject, and imaging means for capturing an image of the inside of the subject, the light distribution matching means including a mirror that reflects the first and second light and a half mirror that reflects a part of the first and second light and transmits a part of the light, the mirror and the half mirror being disposed apart from each other so that a reflection region is formed therebetween, and the first and second light sources being disposed between the mirror and the half mirror;

a communication device disposed on the outside of the subject; and a display device that displays an image by using image data, wherein:

the body-introducable apparatus has wireless transmitting means for transmitting image data obtained by the imaging means as a wireless signal, the communication device includes wireless receiving means for receiving the image data transmitted from the wireless transmitting means, image signal processing means for processing the image data received by the wireless receiving means, and communication device external interface means for storing the image data processed by the image signal processing means to a portable recording medium detachably connected to the communication device, and the display device includes display device external interface means to which the portable recording medium can be detachably connected, and display means for reading the image data from the portable recording medium connected to the display device external interface means and displaying the read image data.

8. A medical system comprising:

a body-introducable apparatus including:

a light source unit having a first light source that outputs first light and a second light source that outputs second light in a wavelength band different from that of the first light, a light distribution matching unit that matches distributions of the first light and the second light, an illuminating control unit that drives the light source unit to illuminate the inside of the subject, and an imaging unit that captures an image of the inside of the subject, the light distribution matching unit including a mirror that reflects the first and second light and a half mirror that reflects a part of the first and second light and transmits a part of the light, the mirror and the half mirror being disposed apart from each other so that a reflection region is formed therebetween, and the first and second light sources being disposed between the mirror and the half mirror;

a communication device disposed on the outside of the subject; and a display device that displays an image by using image data, wherein:

the body-introducable apparatus has a wireless transmitting unit that transmits image data obtained by the imaging unit as a wireless signal, the communication device includes a wireless receiving unit that receives the image data transmitted from the wireless transmitting unit, an image signal processing unit that processes the image data received by the wireless receiving unit, and a communication device external interface unit that outputs the image data processed by the image signal processing unit to the display device, and the display device includes a display device external interface unit that inputs the image data output from the communication device external interface unit, and a display unit that displays an image of the inside of the subject by using the image data which is input to the display device external interface unit.

9. A medical system comprising:

a body-introducable apparatus including:

light source means having a first light source that outputs first light and a second light source that outputs second light in a wavelength band different from that of the first light, light distribution matching means for matching distributions of the first light and the second light, illuminating control means for driving the light source means to illuminate the inside of the subject, and imaging means for capturing an image of the inside of the subject, the light distribution matching means including a mirror that reflects the first and second light and a half mirror that reflects a part of the first and second light and transmits a part of the light, the mirror and the half mirror being disposed apart from each other so that a reflection region is formed therebetween, and the first and second light sources being disposed between the mirror and the half mirror;

a communication device disposed on the outside of the subject; and a display device that displays an image by using image data, wherein:

the body-introducable apparatus has wireless transmitting means for transmitting image data obtained by the imaging means as a wireless signal, the communication device includes wireless receiving means for receiving the image data transmitted from the wireless transmitting means, image signal processing means for processing the image data received by the wireless receiving means, and communication device external interface means for outputting the image data processed by the image signal processing means to the display device, and the display device includes display device external interface means to which the image data output from the communication device external interface means is input, and display means for displaying an image of the inside of the subject by using the image data input to the display device external interface means.

* * * * *